United States Patent
Saleh et al.

(10) Patent No.: US 9,012,492 B2
(45) Date of Patent: Apr. 21, 2015

(54) APOCYNIN-LIPOIC ACID CONJUGATES AND USES THEREOF

(71) Applicant: University of Prince Edward Island, Charlottetown (CA)

(72) Inventors: Tarek Saleh, Stratford (CA); Desikan Rajagopal, Columbus, OH (US); Bobby Khan, Alpharetta, GA (US); Barry James Connell, Charlottetown (CA)

(73) Assignee: University of Prince Edward Island (CA)

( * ) Notice: Subject to any disclaimer, the term of this patent is extended or adjusted under 35 U.S.C. 154(b) by 0 days.

(21) Appl. No.: 14/358,571

(22) PCT Filed: Nov. 15, 2012

(86) PCT No.: PCT/CA2012/001034
§ 371 (c)(1),
(2) Date: May 15, 2014

(87) PCT Pub. No.: WO2013/071400
PCT Pub. Date: May 23, 2013

(65) Prior Publication Data
US 2014/0315989 A1 Oct. 23, 2014

Related U.S. Application Data

(60) Provisional application No. 61/560,089, filed on Nov. 15, 2011.

(51) Int. Cl.
*A61K 31/385* (2006.01)
*C07D 339/04* (2006.01)
*C07C 323/52* (2006.01)

(52) U.S. Cl.
CPC ........... *C07D 339/04* (2013.01); *C07C 323/52* (2013.01)

(58) Field of Classification Search
USPC .............................................. 514/440; 549/39
See application file for complete search history.

(56) References Cited

PUBLICATIONS

International Search Report in Corresponding PCT/CA2012/001034, mailing date Mar. 7, 2013 (5 pages).
Di Stefano, Antonio, et al. "L-Dopa- and Dopamine-(R)-α-Lipoic Acid Conjugates as Multifunctional Codrugs with Antioxidant Properties", Journal of Medicinal Chemistry, 2006, 1486-1493 (8 pages).

*Primary Examiner* — Taofiq A Solola
(74) *Attorney, Agent, or Firm* — Hovey Williams LLP

(57) ABSTRACT

The present application relates to novel apocynin-lipoic acid covalent conjugates, compositions comprising these compounds and their use, in particular for the treatment of diseases, disorders or conditions that are mediated by oxidative stress. In particular, the present application includes compounds of Formula (I), and compositions and uses thereof.

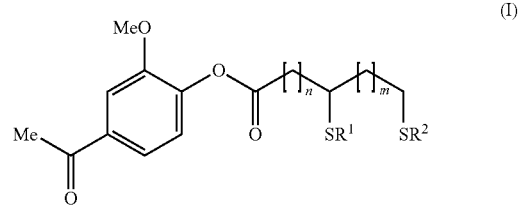

19 Claims, 21 Drawing Sheets

A

B

A

B

A

B

A

B

C

D

A

B

APOCYNIN-LIPOIC ACID CONJUGATES AND USES THEREOF

CROSS-REFERENCE TO RELATED APPLICATIONS

The present application is the National Stage of International Patent Application No. PCT/CA2012/001034, filed Nov. 15, 2012, which claims the benefit of priority from U.S. provisional application No. 61/560,089 filed on Nov. 15, 2011, the contents of which are incorporated herein by reference in their entirety.

FIELD OF THE APPLICATION

The present application relates to novel apocynin-lipoic acid conjugates, compositions comprising these compounds and their use, in particular for the treatment or prevention of diseases, disorders or conditions that are mediated by oxidative stress.

BACKGROUND OF THE APPLICATION

Reactive oxygen species (ROS) play an important role in the development of neurovascular diseases, including stroke, dementia, multiple sclerosis, and Parkinson's disease. This is due, in large part, to excess production of oxidants, decreased nitric oxide (NO) bioavailability, and decreased antioxidant capacity in the vasculature of the central nervous system.[1-4]

A major source for vascular ROS is a family of nonphagocytic NAD(P)H (nicotinamide adenine dinucleotide phosphate) oxidases, including the prototypic Nox2 homolog-based NAD(P)H oxidase.[5] NAD(P)H oxidase-derived ROS plays a physiological role in the regulation of endothelial function and vascular tone and a pathophysiological role in multiple processes, including endothelial dysfunction, inflammation, hypertrophy, and apoptosis which could affect cardiovascular and neurovascular remodeling.[5] These findings have evoked considerable interest because of the possibilities that therapies against nonphagocytic NAD(P)H oxidase may decrease ROS generation. Additionally, strategies to increase nitric oxide (NO) availability and antioxidants may be useful in minimizing vascular injury and inflammation and thereby prevent or regress target organ damage associated with cognitive dementia, including hypertension, dyslipidemia, and diabetes.

The enzyme NADPH oxidase is a membrane-bound enzyme complex. It can be found in the plasma and phagosome membranes.[7] NADPH oxidase is made up of five phagocytic oxidase subunits ("phox", including p22, p40, p47, p67, and p90 phox) and a Rho guanosine triphosphatase.[8] Under normal circumstances, NADPH oxidase is latent in neutrophils and enzymatic activation occurs to assemble in the membranes during respiratory burst. The enzyme generates superoxide by transferring electrons from NADPH inside the cell across the membrane and coupling these to molecular oxygen to produce the superoxide, which is a reactive free-radical.[5] Superoxide can be produced in phagosomes, which contain ingested bacteria and fungi, or it can be produced outside of the cell. In a phagosome, superoxide can spontaneously form hydrogen peroxide that will undergo further reactions to generate reactive oxygen species (ROS).

As noted above, NADPH oxidase is associated with vascular and inflammatory diseases, and NADPH oxidase inhibitors may reverse these processes.[9] NADPH oxidase produces ROSs, and these molecules activate an enzyme that makes the macrophages adhere to the artery wall (by polymerizing actin fibers). This process is counterbalanced by NADPH oxidase inhibitors and by antioxidants.[10-12] For example, NADPH oxidase can be inhibited by apocynin and diphenyleneiodonium (DPI) by preventing the assembly of its subunits.[13] In vitro studies have found that apocynin and DPI depolymerize the actin, break the adhesions, and allow foam cells to migrate out of the intima.[14, 15]

There is considerable interest in the antioxidative and anti-inflammatory effects of phenolic compounds from different botanical sources.[16, 17] Oxidative mechanisms are associated with central nervous system disorders such as stroke and dementia. The evaluation of neuroprotective effects of phenolic compounds are gaining considerable interest as therapeutic agents.[18-20] Some examples include resveratrol from grape and red wine, curcumin from turmeric, apocynin from *Picrorrhiza kurroa*, and epi-gallocatechin from green tea.[21, 22] Increased production of reactive oxygen species (ROS) has been implicated in various chronic diseases, including neurodegenerative diseases.[23] Oxidative stress is implicated in endothelial dysfunction, inflammation, hypertrophy, apoptosis, fibrosis, angiogenesis, and rarefaction.[24]

Apocynin (4-hydroxy-3-methoxyacetophenone) is a major active ingredient from the rhizomes of *Picrorrhiza kurroa*, a botanical plant used as an herbal medicine for potential treatment of a number of inflammatory diseases. Recently, apocynin is regarded as a specific inhibitor for NADPH oxidase in cell and animal models. In vitro studies indicate conversion of apocynin to diapocynin in the presence of peroxidases, e.g., myeloperoxidase, posing the possibility that diapocynin also contributes to the anti-oxidative action of apocynin.[45]

Alpha lipoic acid (LA) is a naturally occurring eight-carbon fatty acid that is synthesized by plants and animals, including humans. The natural configuration is "R", although the RS (DL) lipoic acid is extensively used commercially.[26] It is chemically named 1,2-dithiolane-2-pentanoic acid (also referred to as thioctic acid). It is an important cofactor in the mitochondrial respiratory chain and serves as a cofactor for many enzyme reactions.[27-29] It has also emerged as a potent antioxidant, antiinflammatory, and a mitochondrial protective agent.[30] Both the parent compounds as well as the dihydro form (both the sulfur atoms reduced to thiol functions) have been reported to have antioxidant properties.[26] LA has been reported to lower serum triglycerides, increase glucose uptake by cells, stimulate neurological function, decrease liver toxicity, increase levels of glutathione and ascorbic acid and decrease the expression of inflammatory molecules.[31-34] LA has also been shown to have a neuroprotective effect.[43, 44] LA has a very short half-life in the bloodstream as it undergoes rapid metabolism in the liver.[72] Dosing 3-4 times daily is necessary to accomplish reasonable blood levels. This rather limited bioavailability of LA could be extended by suitably incorporating chemical groups to attenuate the metabolic process in the liver.[35, 36]

It was recently demonstrated in humans that the combination of LA with the angiotensin receptor blocker irbesartan markedly reduced pro-inflammatory soluble IL-6 and VCAM-1 levels and improved vascular endothelial function.[37] Covalent linkage of LA with ibuprofen has been demonstrated to be neuroprotective in rodent models of Alzheimer's disease in which administration of the co-drug decreased the oxidative damage due to the infusion of Aβ (1-40).[48] In addition, a co-drug produced by chemically linking LA with L-Dopa, or dopamine, decreased neuronal oxidative damage associated with the administration of L-Dopa or dopamine alone.[49]

SUMMARY OF THE APPLICATION

New chemical entities that link apocynin and lipoic acid have been prepared and shown to have biological activity indicative of NADPH inhibition as well as neuroprotective effects in a rodent model for reperfusion injury following stroke. In specific assays, these new compounds were shown to have greater activity than apocynin and other known NADPH oxidase inhibitors such as those reported by Zhang et al.[73]

Accordingly the present application includes a compound that is a covalent conjugate between alpha lipoic acid (LA), or a derivative thereof, and apocynin, or a derivative thereof. It will be appreciated that there are several available methods for covalently linking LA and apocynin. In one embodiment of the application, LA and apocynin are linked by covalently bonding the phenol hydroxy group of apocynin with the carboxylic acid group of LA. Therefore, the present application includes a compound of Formula I:

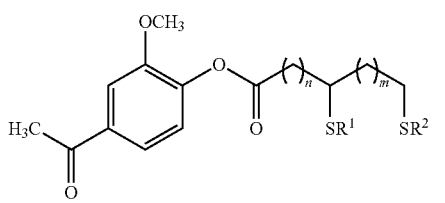

(I)

wherein
n is 1, 2, 3, 4, 5 or 6;
m is 0, 1 or 2;
$R^1$ and $R^2$ are independently selected from the group consisting of H, $C_{1-6}$alkyl and $C(O)C_{1-6}$alkyl, or
$R^1$ and $R^2$ are absent and the two sulfur atoms are bonded together to form, together with the carbon atoms between them, a 4, 5 or 6 membered ring, or a pharmaceutically acceptable salt and/or solvate thereof.

The present application also includes a composition comprising one of more of the compounds of the application and a carrier. In an embodiment, the composition is a pharmaceutical composition comprising one or more compounds of the application and a pharmaceutically acceptable carrier.

In a further embodiment, the compounds of the present application are used as medicaments. Accordingly the application also includes a compound of the application for use as a medicament.

The compounds of the application have been shown to have antioxidant (NADPH oxidase inhibition) and neuroprotectant effects. In embodiments of the application, these effects were shown to be greater for the compounds of the invention than for apocynin and lipoic acid on their own. Accordingly, in embodiments, synergy in activity exists for compounds of the application. Therefore these compounds are useful for treating diseases, disorders or conditions that are mediated by oxidative stress. Accordingly, the present application also includes a method for treating or preventing diseases, disorders or conditions mediated by oxidative stress comprising administering a therapeutically effective amount of one or more compounds of the application to a subject in need thereof. In embodiments of the application, the diseases, disorders or conditions mediated by oxidative stress are those that are the result of reactive oxygen species (ROS). Examples of such diseases, disorders or conditions include, for example, reperfusion injury following stroke, neurodegenerative diseases, inflammatory diseases and neurovascular disorders. Examples of neurodegenerative diseases include dementia, Multiple Sclerosis and Parkinson's disease. Examples of neurovascular disorders include stroke, myocardial infarction, heart failure and renal failure. Examples of inflammatory diseases or disorders include collagen vascular diseases, metabolic disorders and cardiac disease.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The application will now be described in greater detail with reference to the drawings in which:

FIG. 13A shows the intrinsic clearance of the compound of Formula (Ia). FIG. 13B shows the intrinsic clearance of lipoic acid. FIG. 13C shows the intrinsic clearance of apocynin. FIG. 13D shows the intrinsic clearance of diclofenac (positive control).

FIG. 14A shows the intrinsic clearance of the compound of Formula (Ia). FIG. 14B shows the intrinsic clearance of lipoic acid. FIG. 14C shows the intrinsic clearance of apocynin. FIG. 14D shows the intrinsic clearance of diclofenac (positive control for HLM). FIG. 14E shows the intrinsic clearance of verapamil (positive control for DLM).

DETAILED DESCRIPTION OF THE APPLICATION

I. Definitions

Figure 1:
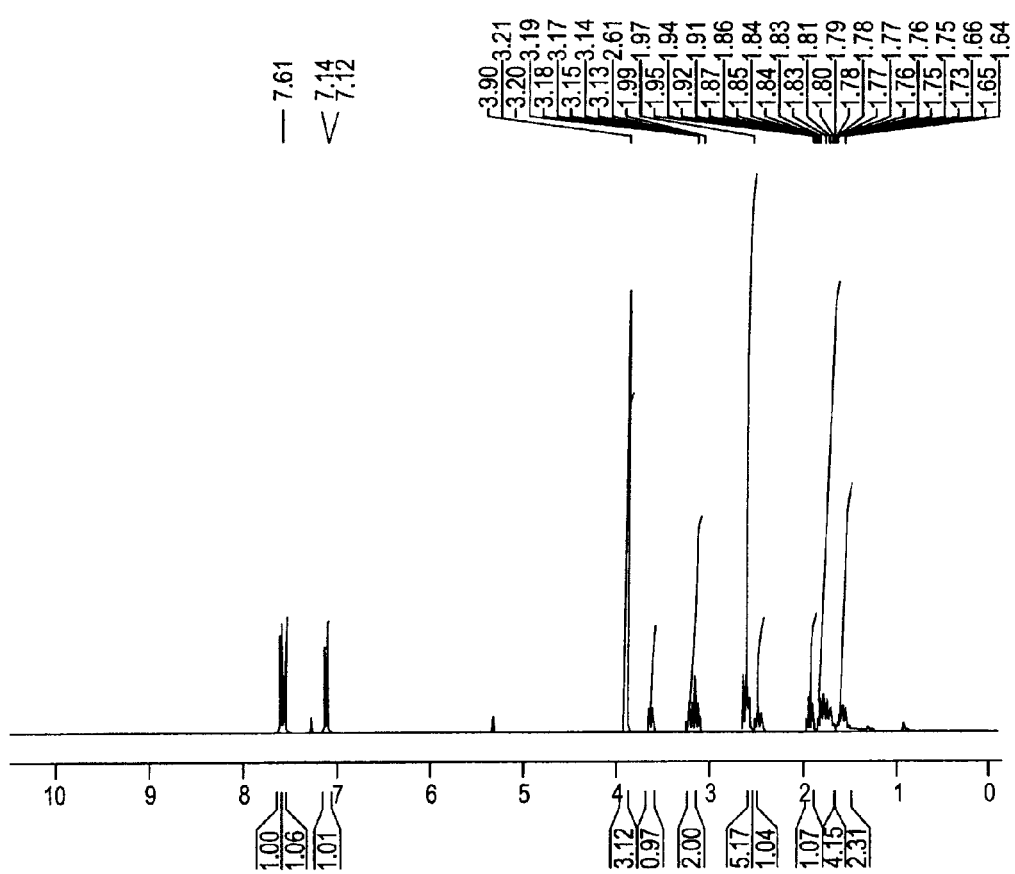
FIG. 1A shows an exemplary $^1$H NMR spectrum of the compound of Formula (Ia), an exemplary compound of the application.
FIG. 1B shows an exemplary High Resolution Mass Spectrum of the compound of Formula (Ia).
Figure 1:
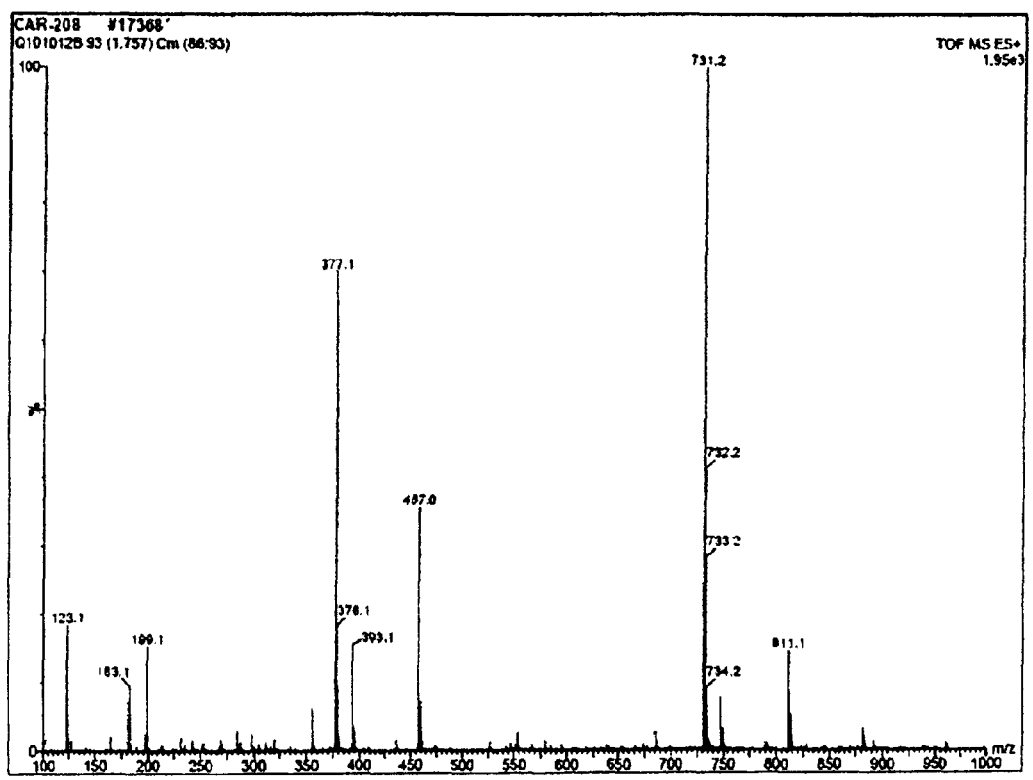

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "alkyl" as used herein, whether it is used alone or as part of another group, means straight or branched chain, saturated alkyl groups. The term $C_{1-6}$alkyl means an alkyl group having 1, 2, 3, 4, 5, or 6 carbon atoms.

The term "compounds of the application" or "compounds of the present application" as used herein refers to a compound of Formula I or a pharmaceutically acceptable salt and/or solvate thereof.

The term "derivative" as used herein refers to a compound that is derived from a parent compound by modification of one or more of the functional groups in the parent molecule. For example, a derivative of LA may be a reduced form (dithiol) of LA, or a reduced form in which the thiol groups are substituted with, for example, a $C_{1-6}$alkyl group or a $C_{1-6}$acyl group. Further, a derivative of apocynin may be a compound wherein the keto group is oxidized (for example to the α-ketoacid) or reduced (to the corresponding alcohol).

The term "subject" as used herein includes all members of the animal kingdom including mammals, and suitably refers to humans.

The term "pharmaceutically acceptable" means compatible with the treatment of subjects, in particular humans.

The term "pharmaceutically acceptable salt" means an acid addition salt which is suitable for, or compatible with, the treatment of patients.

The term "acid addition salt which is suitable for, or compatible with, the treatment of patients" as used herein means any non-toxic organic or inorganic salt of any basic compound. Basic compounds that form an acid addition salt include, for example, compounds comprising a thiol group. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

The formation of a desired compound salt is achieved using standard techniques. For example, the basic compound is treated with an acid in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

In embodiments of the application, the compounds described herein have at least one asymmetric center. These compounds exist as enantiomers Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry. For example, compounds of the application that are shown without any stereochemical designations are understood to be racemic mixtures (i.e. contain and equal amount of each possible enantiomer or diastereomer). However, it is to be understood that all enantiomers and diastereomers are included within the scope of the present application, including mixtures thereof in any proportion.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early cardiovascular disease can be treated to prevent progression, or alternatively a subject in remission can be treated with a compound or composition described herein to prevent recurrence. Treatment methods comprise administering to a subject a therapeutically effective amount of one or more of the compounds of the application and optionally consists of a single administration, or alternatively comprises a series of administrations. As used herein, the term "effective amount" or "therapeutically effective amount" means an amount effective, at dosages and for periods of time necessary to achieve the desired result. For example in the context of treating a disease mediated by oxidative stress, an effective amount is an amount that, for example, reduces oxidative damage compared to the oxidative damage caused without administration of the compound. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

II. Compounds and Compositions of the Application

As noted above, novel compounds having antioxidant activity in assays indicative of NADPH oxidase inhibition as well as in neuroprotectant assays have been prepared. The compounds are derived from apocynin and alpha lipoic acid and are the result of the covalent linkage of these two compounds. Surprisingly, the resulting covalent conjugates showed a significantly enhanced antioxidant effect compared to various known antioxidant compounds (including apocynin) on their own. The compound of Formula (Ia) has been demonstrated to be far superior than either apocynin or lipoic acid alone in its ability to provide neuroprotection when administered during reperfusion in a rat model of ischemia/reperfusion (I/R) injury. The dose of the compound of Formula (Ia) required to produce significant neuroprotection was demonstrated to be many-fold less compared with the doses required for either apocynin or lipoic acid on their own. Accordingly, in an embodiment, the compounds of the application possess synergistic effects.

Accordingly the present application includes a compound that is a covalent conjugate between alpha lipoic acid (LA), or a derivative thereof, and apocynin, or a derivative thereof. It will be appreciated that there are several available methods for covalently linking LA and apocynin. In one embodiment of the application, LA and apocynin are linked by covalently bonding the phenol hydroxy group of apocynin with the carboxylic acid group of LA. Therefore, the present application includes a compound of Formula I:

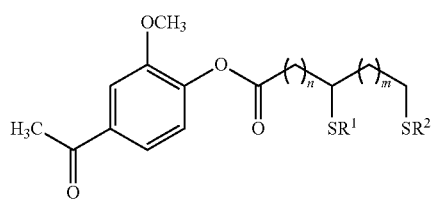

(I)

wherein
n is 1, 2, 3, 4, 5 or 6;
m is 0, 1 or 2;
$R^1$ and $R^2$ are independently selected from the group consisting of H, $C_{1-6}$alkyl and $C(O)C_{1-6}$alkyl, or
$R^1$ and $R^2$ are absent and the two sulfur atoms are bonded together to form, together with the carbon atoms between them, a 4, 5 or 6 membered ring, or a pharmaceutically acceptable salt and/or solvate thereof.

In an embodiment of the application, n is 3, 4 or 5. In another embodiment, n is 4.

In an embodiment of the application, m is 1 or 2. In another embodiment, m is 2.

In an embodiment of the application, $R^1$ and $R^2$ are independently selected from the group consisting of H, $C_{1-4}$alkyl and $C(O)C_{1-4}$alkyl. In another embodiment, $R^1$ and $R^2$ are independently selected from the group consisting of H, $CH_3$ and $C(O)CH_3$. In another embodiment, $R^1$ and $R^2$ are the same. In another embodiment, $R^1$ and $R^2$ are both H.

In an embodiment of the application $R^1$ and $R^2$ are absent and the two sulfur atoms are bonded together to form, together with the carbon atoms between them, a 5 or 6 membered ring. In another embodiment, $R^1$ and $R^2$ are absent and the two sulfur atoms are bonded together to form, together with the carbon atoms between them, a 5 membered ring.

It is another embodiment, that the compound of Formula I is selected from:

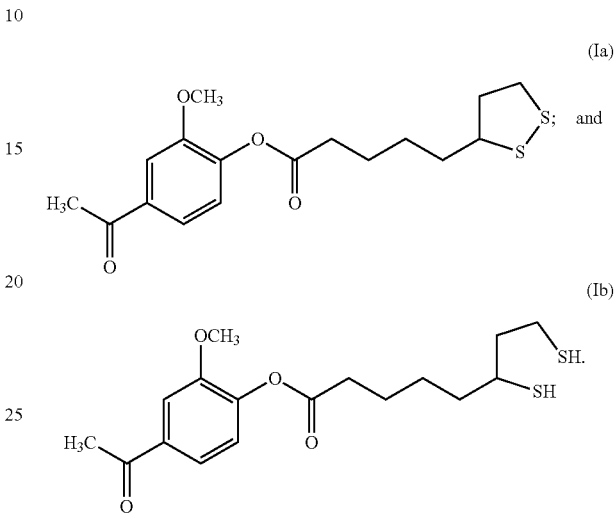

In another embodiment the compound of Formula I is the compound of Formula (Ia)

The compounds of the application are suitably formulated into pharmaceutical compositions for administration to subjects in a biologically compatible form suitable for administration in vivo. Accordingly, the present application also includes a pharmaceutical composition comprising one or more compounds of the application and a pharmaceutically acceptable carrier.

The compounds of the application may be administered to a subject in a variety of forms depending on the selected route of administration, as will be understood by those skilled in the art. A compound of the application may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Conventional procedures and ingredients for the selection and preparation of suitable compositions are described, for example, in Remington's Pharmaceutical Sciences (2000—20th edition) and in The United States Pharmacopeia: The National Formulary (USP 24 NF19) published in 1999.

A compound of the application may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. In an embodiment, coatings that inhibit degradation of the compounds of the application by esterases, for example plasma esterases, are used in the oral administration forms. Timed-release compositions can be formulated, e.g. liposomes or those wherein the active compound is protected with differentially degradable coatings, such as by microencapsulation, multiple coatings, etc. Liposome delivery systems, include, for example, small unilamellar vesicles, large unilamellar vesicles and multilamellar vesicles. Liposomes can be formed from a variety of phospholipids, such as cholesterol, stearylamine or phosphatidylcholines.

It is also possible to freeze-dry the compounds of the application and use the lyophilizates obtained, for example, for the preparation of products for injection.

A compound of the application may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compounds of the application may also be delivered by the use of monoclonal antibodies as individual carriers to which the compound molecules are coupled. Compounds of the application may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Compounds of the application may be used alone or in combination with other known agents useful for treating diseases, disorders or conditions mediated by oxidative stress. Compounds of the application may also be used in combination with agents that inhibit esterases, such as plasma esterases. When used in combination with other agents useful in treating diseases, disorders or conditions mediated by oxidative stress, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of compounds of the application can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. In an embodiment of the application, compositions are formulated for oral administration and the compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. Compounds of the application may be administered in a single daily dose or the total daily dose may be divided into two, three or four daily doses.

III. Methods and Uses of the Application

The compounds of the application have been shown to have antioxidant (NADPH oxidase inhibition) and neuroprotectant effects. Therefore these compounds are useful for treating or preventing diseases, disorders or conditions that are mediated by oxidative stress.

Therefore, the compounds of the present application are useful as medicaments. Accordingly the application also includes a compound of the application for use as a medicament.

The present application includes a method for treating or preventing diseases, disorders or conditions mediated by oxidative stress comprising administering a therapeutically effective amount of one or more compounds of the application to a subject in need thereof.

Also included is a use of one or more compounds of the application for treating or preventing diseases, disorders or conditions mediated by oxidative stress and a use of one or more compounds of the application for preparing a medicament for treating or preventing diseases, disorders or conditions mediated by oxidative stress. Finally, the application also includes one or more compounds of the application for use in treating or preventing diseases, disorders or conditions mediated by oxidative stress.

In embodiments of the application, the diseases, disorders or conditions mediated by oxidative stress are those that are the result of reactive oxygen species (ROS). Examples of such diseases, disorders or conditions include, for example, reperfusion injury following stroke, neurodegenerative diseases, inflammatory diseases and neurovascular disorders. Examples of neurodegenerative diseases include dementia, Multiple Sclerosis and Parkinson's disease. Examples of neurovascular disorders include stroke, myocardial infarction, heart failure and renal failure. Examples of inflammatory diseases or disorders include collagen vascular diseases, metabolic disorders and cardiac disease.

Treatment or prevention methods comprise administering to a subject or a cell, a therapeutically effective amount of one or more of the compounds of the application, and optionally consists of a single administration, or alternatively comprises a series of administrations. For example, the one or more compounds of the application are administered in a single administration any time prior to or following the onset of the disease, disorder or condition. For example, the one or more compounds of the application are administered immediately prior to the onset of the disease, disorder or condition or about 24 hours prior to the onset of the disease, disorder or condition, or any time in between. Alternatively, the one or more compounds of the application are administered immediately following the onset of the disease, disorder or condition or about 48 hours following the onset of the disease, disorder or condition, or any time in between, for example about 1 minute, about 10 minutes, about 30 minutes, about 1 hour, about 5 hours, about 10 hours, about 20 hours, about 24 hours, about 30 hours or about 36 hours, following the onset of the disease, disorder or condition.

However, in another embodiment, the compounds may be administered to the subject or cell in a series of administrations, for example about 1, 2, 3, 4, 5 or 6 times daily for 1 day to about 10 days either before or after the onset of the disease, disorder or condition. The length of the treatment period depends on a variety of factors, such as the cause of the disease, disorder or condition, severity of the disease, disorder or condition, the age of the subject, the concentration of the compound, the activity of the compound, and/or a combination thereof. It will also be appreciated that the effective dosage of the compound used for the treatment or prevention may increase or decrease over the course of a particular treatment or prevention regime. Changes in dosage may result and become apparent by standard diagnostic assays known in the art. In some instances, chronic administration may be required. For example, the compounds are administered to the subject in an amount and for a duration sufficient to treat the subject.

The following non-limiting examples are illustrative of the present application:

EXAMPLES

Example 1

Preparation of the Compound of Formula (Ia)

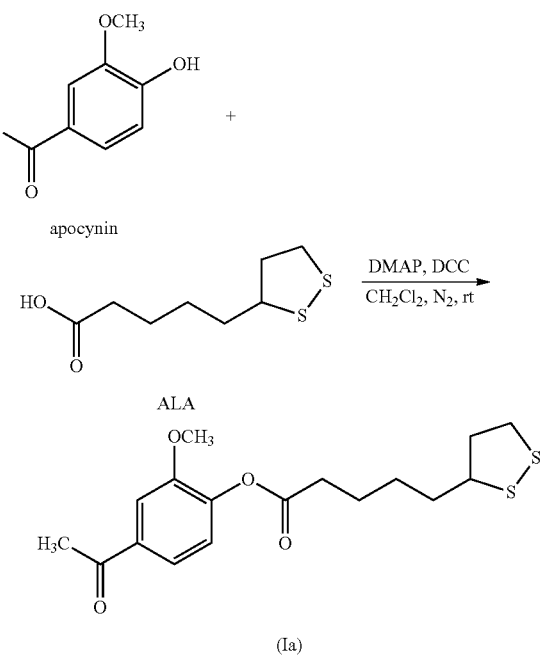

Apocynin (0.01M) was taken in a well dried 100 mL round bottom flask followed by (0.01M) of lipoic acid (LA), and 0.01M of dimethylaminopyridine (DMAP) in 50 mL anhydrous dichloromethane ($CH_2Cl_2$). The dicyclohexylcarbodiimide (DCC) (0.01 M) was added in small quantities over a period of 45 minutes. The entire reaction was performed under a nitrogen atmosphere. After overnight stirring, the pure compound was purified using silica column chromatography after an aqueous work up. The pure compound (Ia) was characterized by proton ($^1H$) nuclear magnetic resonance spectroscopy and mass spectrometry. The $^1H$ NMR spectrum is shown in FIG. 1A. The high resolution mass spectrum is shown in FIG. 1B.

Example 2

In Vitro Testing of the Compound of Formula (Ia)

Compound (Ia) was examined for its effects in inhibiting NADPH oxidase. Specifically, the effects of (Ia) on oxidative stress in N27 neuronal cells, a dopaminergic cell line were studied. N27 cells were exposed to tert-butyl hydrogen peroxide (100 µM) for a 6 hour period.

In separate studies, cells were pretreated with compound (Ia) (100 µM), apocynin (100 µM), or DPI (10 µM) and then exposed to hydrogen peroxide (1 mM). The cells were then lysed, and DNA fragmentation was determined by ELISA assay. As shown in Table 1, DNA fragmentation induced by hydrogen peroxide was reduced by 73% with (Ia) pretreatment, 41% with apocynin pretreatment, and 48% with DPI pretreatment. This effect with (Ia) was more significant than results observed with apocynin or DPI.

Example 3

In Vivo Testing of the Compound of Formula (Ia)

Figure 2:
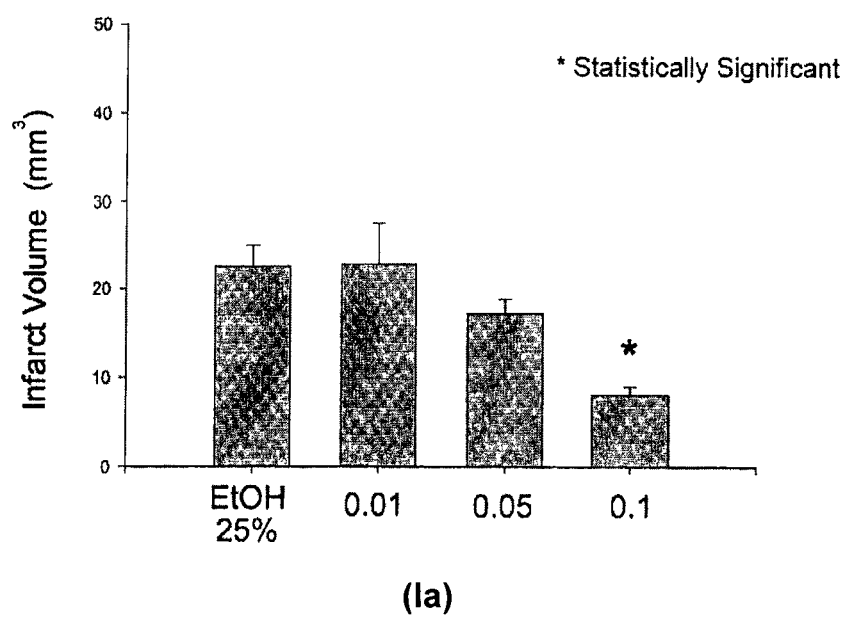
FIG. 2 shows the infarct volume as a function of dose of the compound of Formula (Ia) in Sprague-Dawley rats that were treated with the compound of Formula (Ia) (10-100 µM) for 30 minutes after which the middle cerebral artery (MCA) was occluded to induce a stroke. Animals were sacrificed and stroke infarct volume was measured (n=4 animals). 25% Ethanol was used as a control.

Sprague-Dawley rats were used to study the effects of (Ia) on reperfusion injury following stroke in a rodent model. The rats were anesthetized, and injected with (Ia) (0.01-0.1 mg/kg). After 30 minutes, occlusion of the middle cerebral artery (MCA) was performed. In comparison to ethanol vehicle, there was a dose-dependent reduction in stroke infarct volume with (Ia) (FIG. 2). Blood pressure was measured continuously over a 6 hour period, and there was no change in systemic blood pressure.

Example 4

In Vitro Nitric Oxide Release Assay

Nitric oxide can nitrate the tyrosine residues in bovine serum albumin (BSA) resulting in a yellow color which can be quantified by UV-Vis spectrophotomer.[39] Western blot analysis using tyrosine antibody can also be used. Antibodies are available that detect nitrated proteins in vivo. The nitroso compounds are incubated with albumin and the treated albumin subjected to Western blot analysis using a nitrotyrosine antibody. Untreated albumin will have no detectable nitrotyrosine whereas the samples incubated with nitroso compounds show intense reactivity with the antibody. After incubation the samples are separated on SDS-PAGE electrophoresis with markers of molecular weight. At the end of the electrophoresis, the blot is transferred on to nitrocellulose membrane and a Western blot is performed using anti-nitrotyrosine antibodies at a 1:1000 dilution.

Example 5

In Vivo Efficacy in Neurovascular Diseases

For in-vivo efficacy in neurovascular diseases, the effects of the compounds of the application can be studied using the dementia SAMP-8 mouse model. This animal model is selected owing to the rapid progression of events in this model (morbidity and mortality) that will allow Kaplan Meier type analysis. The SAMP-8 mice develop early abnormalities in learning and memory. These are related to abnormalities in septohippocampal function with a decrease in serotonin leading to an increase in GABA and a decrease in acetylcholine. The cognitive defects in these animals are due to overproduction of beta-amyloid and can be reversed by antibodies to beta-amyloid or specific antisense oligonucleotides. The major defect produced by beta-amyloid in these mice appears to be reduction in delta9 desaturase activity leading to altered membrane phospholipid content.[40] The SAMP-8 mouse appears to be an excellent model to examine the pathophysiology of early defects seen in cognitive dementia and Alzheimer disease. The genes and proteins can be functionally categorized into neuroprotection, signal transduction, protein folding/degradation, cytoskeleton/transport, immune response and reactive oxygen species (ROS) production. All of these processes are involved in learning and memory. Although these studies provide insight into the mechanisms that contribute to the learning and memory decline in aged SAMP-8 mice, higher throughput techniques of proteomics and genomics are used to study the alterations of gene expression and protein abnormalities in SAMP-8 mice brains in order to more completely understand the central nervous system dysfunction in this mouse model.[41]

The experimental protocol for the SAMP-8 mouse model is presented in Table 2. The brain, aortic arch, kidney, heart and liver tissue will be homogenized and stored at −70° C. for performance of immunoblots. The testing proposed above and in Table 2 will test key vascular end-points of interest in the pathology involved in cognitive dementia.

Example 6

Other In Vitro Cell Culture Experiments for the Compounds of the Application a) Endothelial Inflammatory Gene Expression Using Human Brain Microvascular Endothelial Cells (HBMEC):

Gene expression is expressed as relative fold change to housekeeping genes (GAPDH, 36B4, Hmg14 etc) validated to not be affected by treatment. PCR efficiency is calculated for all primer sets and the LightCycler 480 software will be used to correct for PCR efficiency between target and housekeeping genes. Primers are designed to span genomic introns thus avoiding amplification of genomic DNA possibly present in the RNA samples.

b) NFκB Activation Assays Using TNF Stimulation of Human Brain Microvascular Endothelial Cells (HBMEC):

HBMECs are grown in cover slips in chambers containing regular media. On attaining 80% confluence, the cells are serum starved for 12 hours and then changed to one containing 10 ng/ml TNFα, or 1 ng/ml bovine serum albumin (vehicle) for 6 hours prior to the actual assessment of nuclear focalization of the p65 sub-unit of NFκB. Distribution of p65 is calculated as intensity in the cytoplasm and nucleus in regions of interest. At least 5 cells per high power field are used and at least 5 high power fields per concentration of the compound are used. FITC labeled antibodies to the p65 sub-unit are used to delineate NFκB while DAPI is used to stain nuclei.

c) In Vitro Antioxidant Effects:

To determine the generic and specific antioxidant nature of the compounds of the application, horse radish peroxidase, soybean 15-lipoxygenase, xanthine oxidase (cytochrome c) and a chemical oxidant (AAPH) are used with appropriate substrates to determine the antioxidant nature of the derivatives.

d) Immunoblots and RT-PCR:

This is performed using standard methodology. Inflammatory gene expression (VCAM-1/ICAM-1/TNF/MCP-1) by RT-PCR and protein expression of eNOS, nNOS and Akt including phosphorylated forms are performed using standard approaches in the laboratory. The expression of the following genes that have shown to be affected in the SAMP-8 mouse is measured: hsp70, hsp90, cyclophillin, actin, and myelin basic protein.[42]

Example 7

In Vivo Testing of the Compound of Formula (Ia) in Rats

There is a limited window of opportunity following cerebral vascular occlusion for thrombolytic therapy to protect against further I/R-induced cell death (4 h following the onset of clinical signs in humans). This represents a critical time frame within which to study the efficacy of neuroprotectants. Also, most cardiovascular consequences following stroke occur within the first 4-6 h after stroke in humans.[57] Therefore, it was the intention of the present study to examine the acute, neuroprotective effects of the compound of Formula (Ia), using a rodent model of I/R recently developed and validated.[46] Tissue harvested from the ischemic cortex in animals pretreated with the compound of Formula (Ia) was examined to determine the effect of the compound of Formula (Ia) on various cellular antioxidant pathways, as is described in greater detail below.

Previous work has provided evidence that preadministration of apocynin and lipoic acid at subthreshold levels for neuroprotection enhanced the neuroprotective capacity when injected in combination.[51] Therefore, the present investigation was designed to determine whether a co-drug consisting of lipoic acid and apocynin functional groups bound by a covalent bond, i.e. the compound of Formula (Ia), is capable of similar efficacy using a rodent model of stroke. As described in greater detail below, male rats were anesthetized with Inactin (100 mg/kg iv), and the middle cerebral artery was occluded for 6 h or allowed to reperfuse for 5.5 h following a 30-min occlusion (ischemia/reperfusion, I/R). Preadministration of the compound of Formula (Ia) dose-dependently decreased infarct volume in the I/R model ($P<0.05$), but not in the middle cerebral artery occlusion model of stroke. Using the optimal dose, the compound of Formula (Ia) was then injected during the stroke or at several time points during reperfusion, and significant neuroprotection was observed when the compound of Formula (Ia) was administered up to 90 min following the start of reperfusion ($P<0.05$). A time course for this neuroprotective effect showed that the compound of Formula (Ia) resulted in a decrease in infarct volume following 2 h of reperfusion compared with vehicle. The time course of this neuroprotective effect was also used to study several mediators along the antioxidant pathway and showed that the compound of Formula (Ia) increased the level of mitochondrial superoxide dismutase and oxidized glutathione and decreased a marker of lipid peroxidation due to oxidative stress (HNE-His adduct formation). While not wishing to be limited by theory, taken together, the data suggest that the compound of Formula (Ia) may utilize similar pathways to those observed for the two parent compounds; apocynin and lipoic acid, however, it may also act through a different mechanism of action.

(a) Materials and Methods

All experiments were carried out in accordance with the guidelines of the Canadian Council on Animal Care and were approved by the University of Prince Edward Island Animal Care Committee.

General Surgical Procedures.

All experiments were conducted on male Sprague-Dawley rats (total of 229 rats; 250-350 g; Charles River, Montreal, PQ, Canada). For all animals, food and tap water were available ad libitum. Rats were anesthetized with sodium thiobutabarbital (Inactin; Sigma-Aldrich; St. Louis, Mo.; 100 mg/kg ip), which provided a stable plane of anesthesia for the full duration of the experimental time period. To monitor blood pressure and heart rate, a polyethylene catheter (PE-50; Clay Adams, Parsippany, N.J.) was inserted into the right femoral artery. For intravenous administration of drugs, a second polyethylene catheter (PE-10; Clay Adams) was inserted into the right femoral vein. Arterial blood pressure was measured with a pressure transducer (Gould P23 ID, Cleveland, Ohio) connected to a Gould model 2200S polygraph. Heart rate was determined from the pulse pressure using a Gould tachograph (Biotach). These parameters were displayed and analyzed using PolyviewPro/32 data acquisition and analysis software (Grass Technologies, Warwick, R.I.). An endotracheal tube was inserted to facilitate breathing. Body temperature was monitored and maintained at $37\pm1°$ C. using a Physitemp feedback system (Physitemp Instruments, Clifton, N.J.).

Middle Cerebral Artery Occlusions.

The detailed methodology for permanent middle cerebral artery occlusion (MCAO) and transient (I/R) occlusion of the middle cerebral artery has been published previously.[46] Briefly, animals were placed in a David Kopf stereotaxic frame (Tujunga, Calif.), and the right middle cerebral artery (MCA) approached through a rostral-caudal incision of the skin and *frontalis* muscle at the approximate level of bregma. Blood flow through the MCA was impeded by the placement of surgical suture behind the MCA at three designated positions along the exposed vessel. The sutures were positioned so that the middle of each suture applied pressure to the underside of the MCA and impeded blood flow as confirmed using laser Doppler flowmetry (OxyFlo, Oxford-Optronix, Oxford, UK; Ref. 46). This three-point placement of surgical sutures produced a highly reproducible and consistent focal ischemic lesion (permanent ischemia) restricted to the prefrontal cerebral cortex. For transient I/R, the sutures were left in place for 30 min and then removed (reperfusion) to allow blood flow to return to the area for an additional 5.5 h (209 rats received I/R). In 12 rats, sutures were left in place for 6 h as a model of permanent ischemia.

Effect of the Compound of Formula (Ia) on Infarct Volume Following Both Transient (I/R) and Permanent MCAO.

To examine the effect of the compound of Formula (Ia) on I/R-induced cell death, injections of the compound of Formula (Ia) (0.01, 0.05, 0.1, or 0.5 mg/kg; 1 ml/kg iv; n=4 per group) or vehicle (25% EtOH; 1 ml/kg iv; n=6) were made 30 min prior to the onset of MCAO. The sutures were left in place for 30 min and removed. Reperfusion was allowed for 5.5 h, and the experiment was terminated.

To examine the effect of the compound of Formula (Ia) on ischemia-induced cell death only, injections of the compound of Formula (Ia) (0.1 or 1.0 mg/kg; 1 ml/kg iv; n=4 per group) or vehicle (25% EtOH; 1 ml/kg iv; n=4) were made 30 min prior to 6 h of permanent MCAO (sutures left in place for 6 h). The concentration of 0.1 mg/kg represents the optimal dose of the compound of Formula (Ia), as determined above, and 1.0 mg/kg represents a 10-fold higher concentration of the optimal dose, as the optimal dose of 0.1 mg/kg was not effective in producing neuroprotection. The experiments were terminated at the end of the 6 h of occlusion.

To determine whether the compound of Formula (Ia) was neuroprotective when administered during the 30-min period of occlusion, injections of the compound of Formula (Ia) at a dose that produced optimal neuroprotection based on the dose-response-curve described above (0.1 mg/kg; 1 ml/kg iv; n=4) or vehicle (25% EtOH; 1 mi/kg iv; n=4) were made 15 min following the onset of MCAO. After a further 15 min, the sutures were removed to allow for an additional 5.5 h of reperfusion.

To examine the effect of the compound of Formula (Ia) on reperfusion injury alone, injections of the optimal dose of the compound of Formula (Ia) (0.1 mg/kg; 1 ml/kg iv; n=4 per group) or vehicle (1 ml/kg iv; n=4 or 5 per group) were made following 30 min of MCAO, immediately prior to the removal of the sutures, or 30, 60, 90, 120, or 180 min following suture removal (start of reperfusion). In all cases, the experiments were terminated following 5.5 h of reperfusion.

To determine whether the compound of Formula (Ia) required bioactivation and/or metabolism to an active intermediate to produce neuroprotection, the effect of direct intracortical injections of the compound of Formula (Ia) on infarct volume were investigated in the present model of transient occlusion (I/R). The compound of Formula (Ia) (0.01, 0.1, 0.5, or 1.0 μM in 200 nl; n=4 per group) or the same volume of vehicle (0.0125% EtOH; 200 n1; n=6) was injected into the ipsilateral hemisphere (bregma—0.3 mm, lateral—5.5 mm and depth of—3.0 mm from the dorsal surface of the brain)[47] 10 min prior to suture placement followed by 30 min of MCAO and 5.5 h of reperfusion.

Effect of the Compound of Formula (Ia) on Baseline Blood Pressure and Heart Rate.

To determine the effect of the compound of Formula (Ia) (0.1 mg/kg; 1 ml/kg; n=4) or vehicle (25% EtOH; 1 ml/kg; n=4) administration on baseline blood pressure and heart rate, continuous recordings of blood pressure and heart rate were taken prior to and following drug or vehicle administration. Further recordings of the parameters were made at 15, 30, 45, 60, 90, and 120 min following drug administration, at which time the experiment was terminated.

Effect of the Compound of Formula (Ia) on Cardiac Baroreceptor Reflex Sensitivity, Blood Pressure, and Heart Rate Following I/R.

To determine the effect of drug administration on autonomic reflex activation, the baroreceptor reflex was evoked using a bolus intravenous injection of the α-adrenergic receptor agonist, phenylephrine-hydrochloride (Sigma-Aldrich; 0.1 ml; 2.5 μg/ml iv). The ratio of the peak change in the magnitude of the reflex bradycardia to the magnitude of the phenylephrine-induced pressor response [ΔHR (heart rate)/ΔMAP (mean arterial pressure)] was used as a measure of baroreceptor reflex sensitivity (BRS). BRS was tested at 10 min and immediately prior to the compound of Formula (Ia) (0.1 mg/kg; 1 ml/kg; n=3) or vehicle (25% EtOH; 1 ml/kg; n=3) administration. BRS was then tested 15 and 30 min following drug administration (prior to MCAO), and then 5, 10, 20, and 30 min during MCAO (30 min MCAO), as well as 10, 20, 30, 60, 90, 120, 150, 210, 270, and 330 min following suture removal. The experiments were terminated after 5.5 h of reperfusion.

Time Course of the Effect of the Compound of Formula (Ia) on Infarct Volume Following I/R.

To examine the effect of the compound of Formula (Ia) on the change in infarct volume over the 5.5 h of reperfusion, injections of the optimal dose of the compound of Formula (Ia) (0.1 mg/kg; 1 ml/kg iv; n=4 per group) or vehicle (25% EtOH; 1 ml/kg iv; n=4) were made 30 min prior to the onset of MCAO. The sutures were left in place for 30 min. Brains were removed, and infarct volume was measured at the end of 30 min of MCAO, or at 30 min, 1, 2, 4, or 5.5 h following reperfusion (n=4 or 5 per group).

Histological Procedures.

At the end of each experiment in which infarct volume was measured, animals were transcardially perfused with PBS (0.1 M; 200 ml), the brains were removed and sliced into 1-mm coronal sections using a rat brain matrix (Harvard Apparatus, Holliston, Mass.). Sections were incubated in a 2% solution of 2,3,5-triphenol tetrazolium chloride (TTC; Sigma-Aldrich) for 5 min. Infarct volumes were calculated with the use of scanned digital images of each brain section. The infarct area for both sides of each brain section was calculated using a computer-assisted imaging system (Scion, Frederick, Md.). The infarct areas for each side for each individual section were averaged and multiplied by the width of each section (1 mm) to give the infarct volume for each section. The sum total of all the individual infarct volumes provided the infarct volume for each rat.

Effect of the Compound of Formula (Ia) on Markers of Oxidative Stress.

To examine the effect of the compound of Formula (Ia) on various markers of oxidative stress throughout the 5.5 h of reperfusion, injections of the optimal dose of the compound of Formula (Ia) (0.1 mg/kg; 1 ml/kg iv; n=5 per group at each time point) or vehicle (25% EtOH; 1 ml/kg iv; n=5 per group at each time point) were made 30 min prior to the onset of MCAO. The sutures were left in place for 30 min. Brains were removed, and cortical tissue was collected at the end of the 30 min of occlusion (no reperfusion), or following 30 min, 1, 2, 4, or 5.5 h of reperfusion. At the end of each time point, animals were perfused transcardially with 200 ml of 100 mM PBS (pH 7.4), and the brains were removed. The ipsilateral cerebral cortex was isolated, and an 8-mm diameter biopsy punch was used to obtain tissue from the ischemic core. The tissue was weighed and homogenized (40% wt/vol) in ice-cold PBS. Aliquots of whole homogenate were frozen at −80° C. immediately for measurements of hydrogen peroxide ($H_2O_2$). The remaining sample was diluted 1:2 with ice-cold PBS and centrifuged at 12,000 g for 15 min at 4° C. Aliquots of the supernatant were stored at −80° C. until assayed for protein levels, superoxide dismutase (SOD1 and SOD2) activity, 4-hydroxynonenal-histidine (HNE-His) adducts (OxiSelect Kits, Cell Biolabs, San Diego, Calif.), reduced glutathione (GSH), oxidized glutathione (GSSG; Cayman Chemical, Ann Arbor Mich.), and cytoplasmic enrichment of DNA fragments (apoptosis) (Roche Diagnostics, Montreal, QC, Canada) using selective assay kits according to manufacturer's specifications.

Statistical Analysis.

Data were analyzed using a statistical software package (SigmaStat and SigmaPlot; Jandel Scientific, Tujunga, Calif.). All data are presented as a means±SE. Differences were considered statistically significant when $P \leq 0.05$ by an ANOVA followed by a Bonferroni post hoc analysis. When only two groups were compared, the Student's t-test was used.

(b) Results

Effect of Preadministration of the Compound of Formula (Ia) on Infarct Volume.

Figure 3:
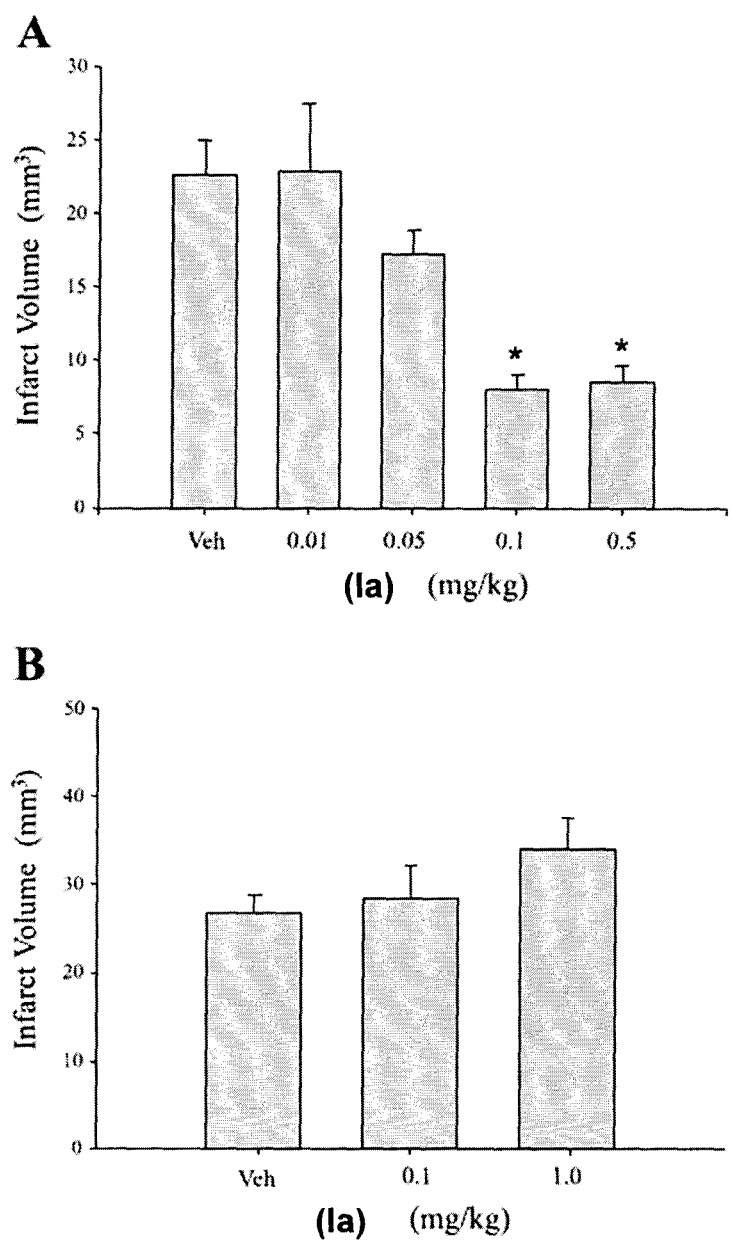
FIG. 3A shows the effect of pretreatment [30 min prior to occlusion of the middle cerebral artery (MCAO)] with the compound of Formula (Ia) (n=4/group) on infarct volume ($mm^3$) calculated from triphenyltetrazolium chloride (TTC)-stained 1-mm thick coronal sections throughout the extent of the infarct following ischemia/reperfusion (I/R). Each bar represents the means±SE. *Significant difference (P≤0.05) from the vehicle group (n=6).
FIG. 3B shows the effect of the compound of Formula (Ia) administered 30 min prior to permanent (6 h) MCAO on infarct volume ($mm^3$) calculated from TTC stained, 1-mm-thick coronal slices throughout the extent of the infarct. Each bar represents the means±SE and n=4/group.

This experiment was designed to determine the effect of the compound of Formula (Ia) preadministration on infarct volume following I/R. Preadministration of the compound of Formula (Ia) resulted in a dose-dependent neuroprotection with a dose of 0.1 and 0.5 mg/kg resulting in a significant decrease in infarct volume compared with the administration of vehicle (Veh) ($P \leq 0.05$; FIG. 3A).

To examine the effect of the compound of Formula (Ia) on ischemia-induced cell death only, injections of the compound of Formula (Ia) (0.1 or 1.0 mg/kg) or vehicle were made 30 min prior to 6 h of MCAO (sutures left in place for 6 h). Neither concentration of the compound of Formula (Ia) (the optimal dose of 0.1 mg/kg, as determined above, or 1.0 mg/kg, a 10-fold increase in the optimal dose) produced significant neuroprotection when infarct volume was measured 6 h following the start of MCAO ($P \geq 0.05$; FIG. 3B).

Effect of Systemic Compound of Formula (Ia) Injection on Blood Pressure and Heart Rate.

The following experiment was designed to determine the effect of the compound of Formula (Ia) on arterial pressure and heart rate for a period of 2 h following administration. Baseline MAP and mean HR prior to drug administration were 112±11 mm/Hg and 388±26 bpm, respectively. Administration of the compound of Formula (Ia) (0.1 mg/kg iv) did not significantly alter mean arterial blood pressure or mean HR at any time point during the 2-h continuous recording compared with vehicle (P≥0.05; data not shown).

Effect of Compound of Formula (Ia) Preadministration on Cardiovascular Parameters Following I/R.

Figure 4:
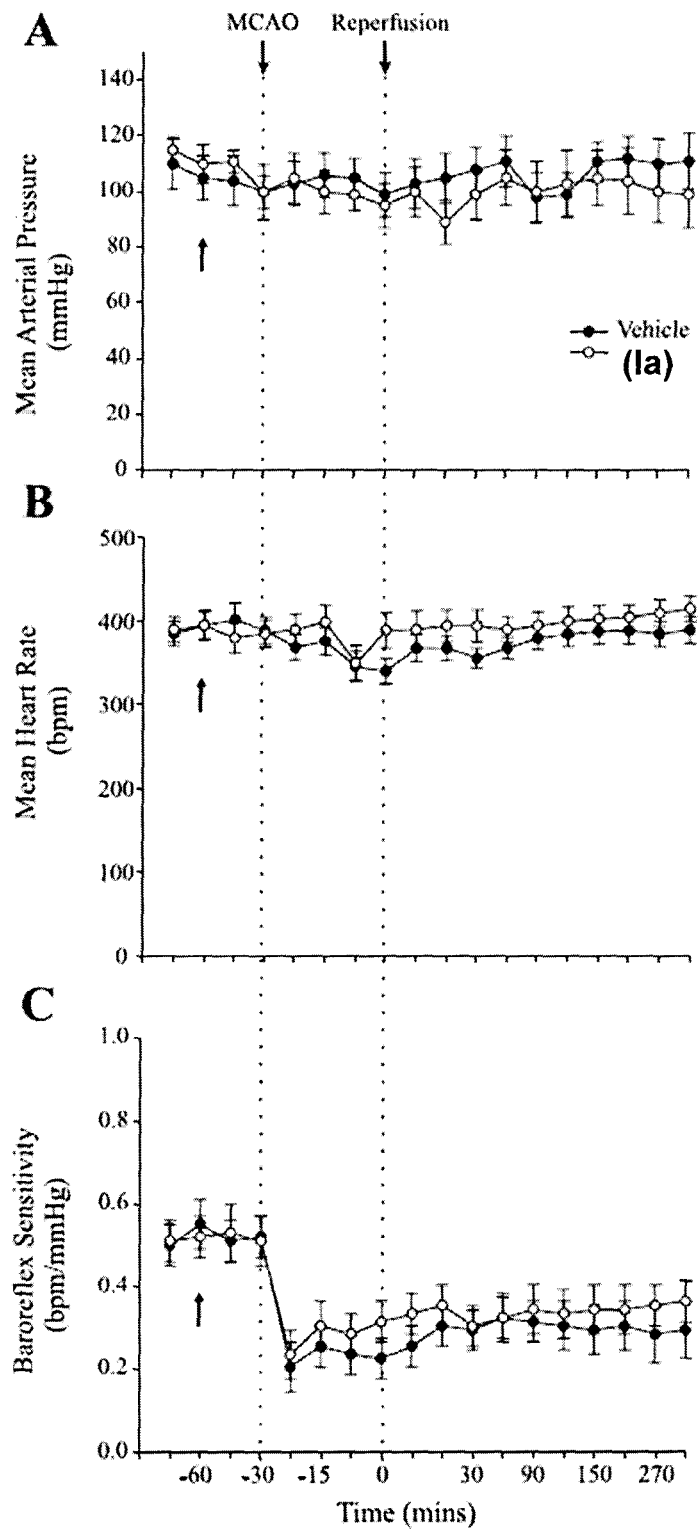
FIG. 4 shows cardiovascular responses to the compound of Formula (Ia) (0.1 mg/kg; n=3) or vehicle (25% EtOH; n=3) pretreatment (iv) 30 min prior to I/R. Graphs represent average changes in mean arterial pressure (A; MAP, mmHg), heart rate (B; HR, bpm), and baroreflex sensitivity (C; BRS, bpm/mmHg) following phenylephrine injection (0.0025 µg/ml iv). The up arrow indicates time of compound of Formula (Ia) or vehicle injection (30 min pre-MCAO). The first dashed line represents the time at which the MCA was occluded, and the second line indicates when blood flow was returned (reperfusion). Each data point represents the mean±SE.

The following experiment was designed to determine the effect of preadministration of the compound of Formula (Ia) on MAP, mean HR, and the mean cardiac BRS before, during, and following 30 min of MCAO. MAP, HR, and BRS prior to compound of Formula (Ia) administration were 119±15 mmHg, 402±22 bpm, and 0.55±0.05 bpm/mmHg, respectively and prior to vehicle administration were 110±9 mmHg, 398±19 bpm, and 0.52±0.05 bpm/mmHg, respectively. These values did not change following compound of Formula (Ia) or vehicle administration prior to MCAO (P≥0.05 for all comparisons; FIGS. 4A-C). During 30 min of MCAO and during 5.5 h of reperfusion, there were no significant differences in the mean arterial pressure or mean heart rate compared with pre-MCAO values (P≥0.05 for both compound of Formula (Ia) and vehicle; FIGS. 4, A and B). However, mean BRS values in both the compound of Formula (Ia) and vehicle groups were equally significantly decreased within 5 min of the beginning of MCAO (0.23±0.05 bpm/mmHg and 0.28±0.08 bpm/mmHg, respectively; P≤0.05 for both groups compared with pre-MCAO values; FIG. 4C) and remained significantly depressed throughout the 30 min of MCAO (P≤0.05 for both groups compared with pre-MCAO values; FIG. 4C). The mean BRS for both groups remained significantly decreased compared with pre-MCAO values throughout the 5.5 h of reperfusion (P≤0.05 at all time points measured for both groups compared with pre-MCAO values; FIG. 4C).

Effect of Compound of Formula (Ia) on Infarct Volume when Administered Either During MCAO or Following the Start of Reperfusion.

Compound of Formula (Ia) or vehicle was injected intravenously at various time points during MCAO or following the start of reperfusion. There were no significant differences in the mean infarct volumes when vehicle was injected during MCAO or at any time point during reperfusion (P≥0.05); therefore, the vehicle data for all time points were pooled (n=29) in FIG. 5. All statistical comparisons were made between the infarct volumes measured following vehicle and compound of Formula (Ia) administration at each time point.

Figure 5:
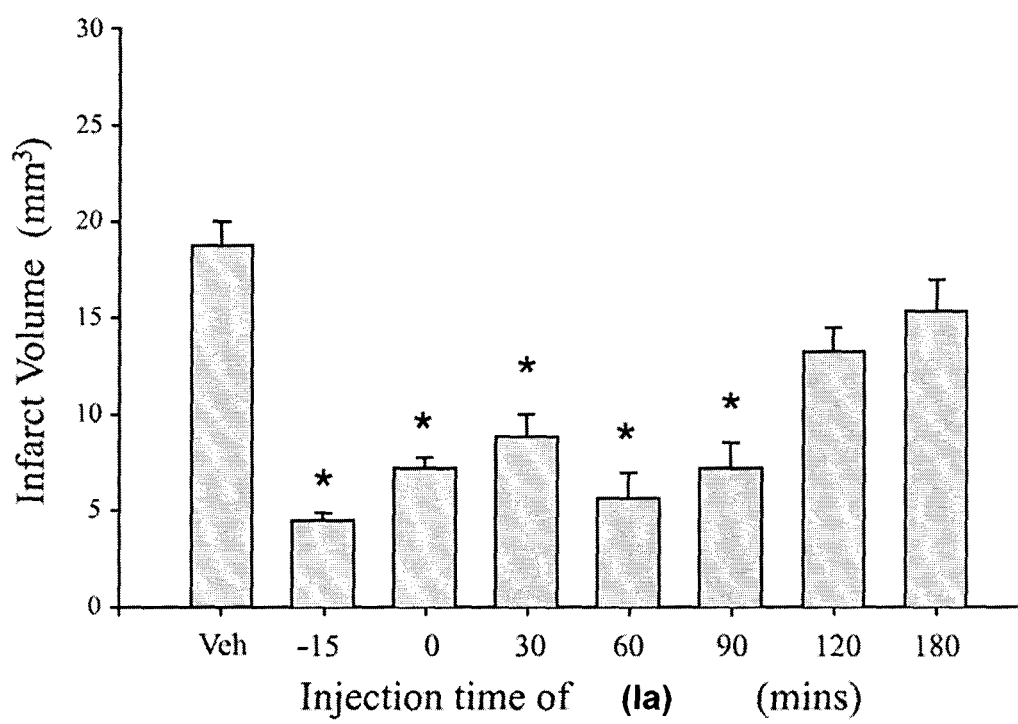
FIG. 5 shows the effect of compound of Formula (Ia) (0.1 mg/kg) or vehicle (0.0125% EtOH) administered 15 min prior to the beginning of reperfusion (−15), immediately prior to suture removal and the start of reperfusion (0), or 30, 60, 90, 120, and 180 min following reperfusion on infarct volume ($mm^3$). Each bar represents the mean±SE (n=4/group). *Significant difference (P≤0.05) from the vehicle control group at the same time point. There were no significant differences in the mean infarct volumes when vehicle was injected during MCAO or at any point during reperfusion (P≥0.05); therefore, the vehicle data for all time points were pooled and are represented by a single bar.

Administration of the compound of Formula (Ia) (0.1 mg/kg iv) 15 min into a 30-min period of MCAO (15 min prior to the start of reperfusion) produced significant neuroprotection compared with vehicle when infarct volume was measured following 5.5 h of reperfusion (P≤0.05; FIG. 5).

The effect of the compound of Formula (Ia) on reperfusion injury only was determined by measuring the infarct volume following drug administration immediately prior to suture removal, or 30, 60, 90, 120, or 180 min following the start of reperfusion. Administration of the compound of Formula (Ia) (0.1 mg/kg) at time 0 (start of reperfusion), and 30, 60, and 90 min following the start of reperfusion resulted in significant decreases in infarct volume compared with vehicle administration (P≤0.05 at each time point; FIG. 5). Administration of the compound of Formula (Ia) (0.1 mg/kg) 120 and 180 min following suture removal did not result in a significant difference in infarct volume compared with the administration of vehicle at those time points (P≥0.05; FIG. 5).

Effect of Intracortical Injections of the Compound of Formula (Ia) on Infarct Volume Following I/R.

Figure 6:
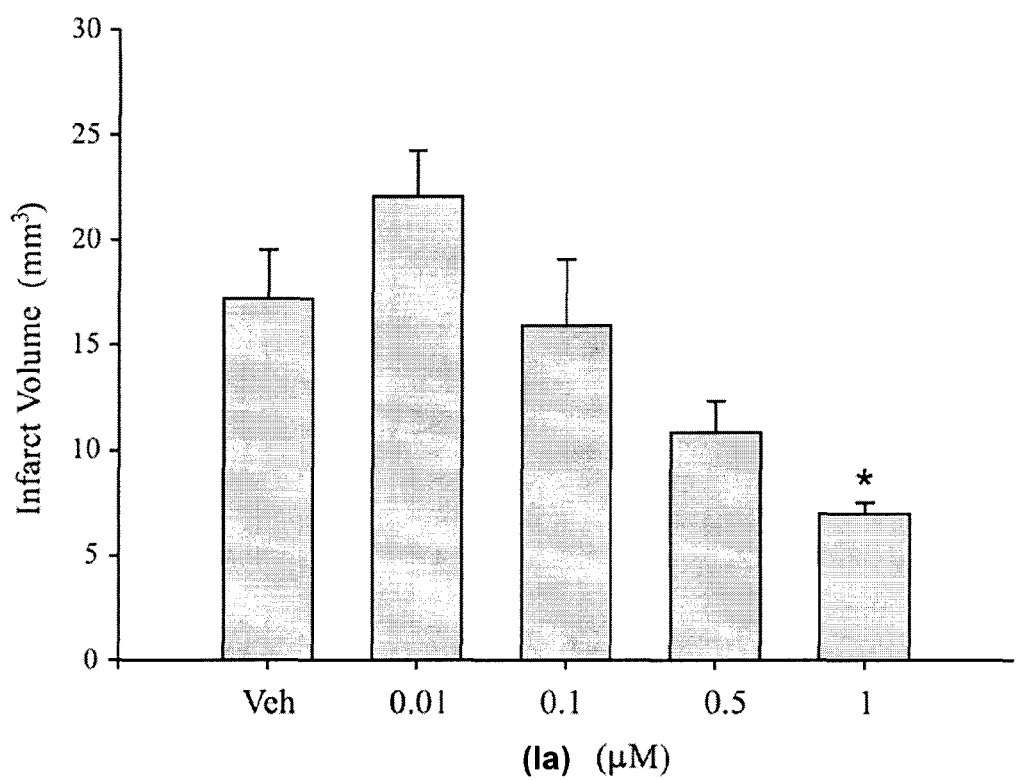
FIG. 6 shows the effect of direct cortical injections of the compound of Formula (Ia) (n=4/group) or vehicle (0.0125% EtOH; n=6) 10 min pre-MCAO on infarct volume (mm$^3$) calculated from TTC-stained 1-mm-thick coronal sections throughout the extent of the infarct following I/R. Each bar represents the mean±SE. *Significant difference (P≤0.05) from the vehicle control group.

This experiment was designed to determine the effect of direct cortical preinjection with the compound of Formula (Ia) on infarct volume following I/R. Compound of Formula (Ia) preinjection resulted in a dose-dependent neuroprotection with a dose of 1.0 μM resulting in a significant decrease in infarct volume compared with the intracortical preinjection of vehicle (P≤0.05; FIG. 6).

Time Course for the Effect of the Compound of Formula (Ia) on Infarct Volume.

Figure 7:
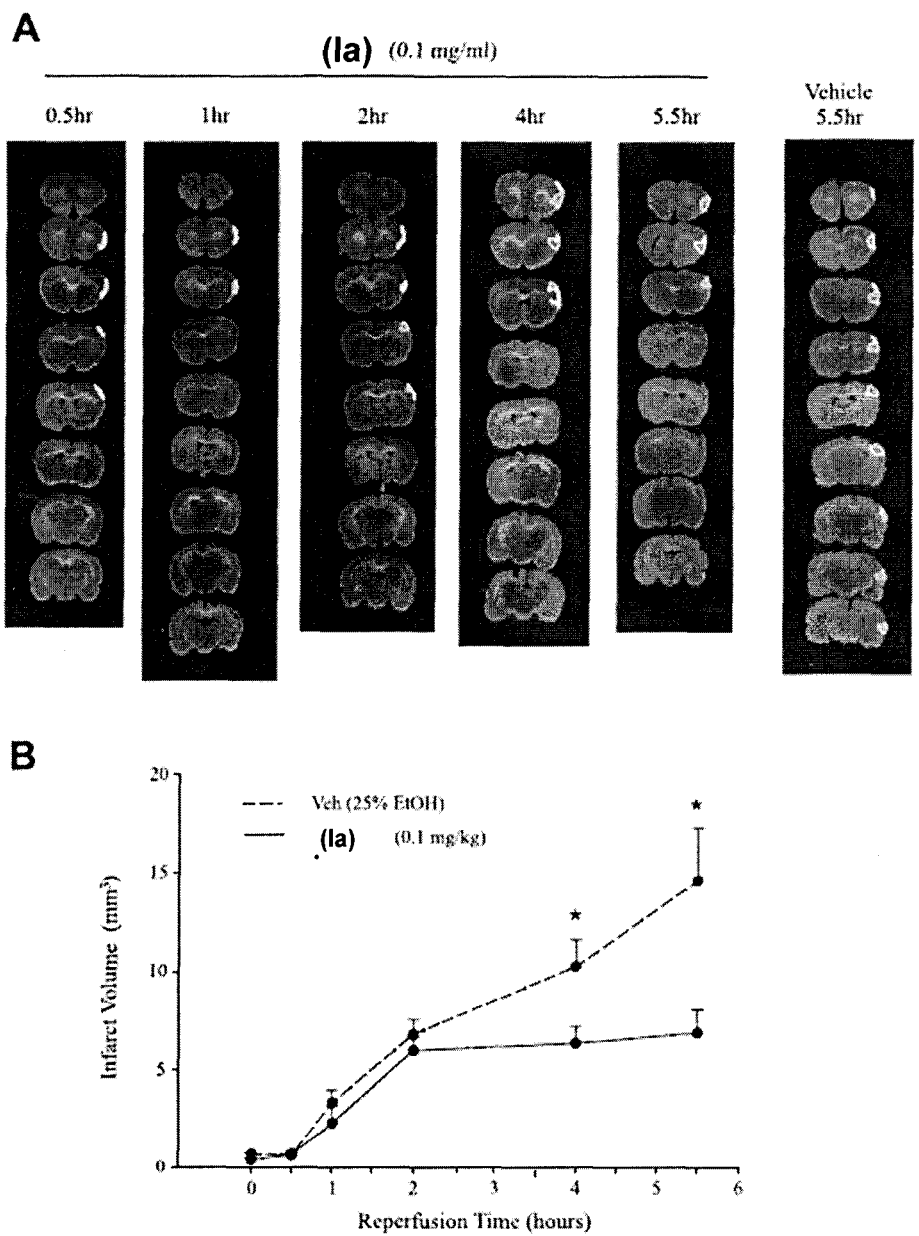
FIG. 7A shows representative digital photomicrographs of TTC-stained 1-mm-thick coronal sections following 30 min of MCAO, illustrating the extent of the infarct size within the prefrontal cortex at progressive time points during 5.5 h of reperfusion in vehicle (25% EtOH) and compound of Formula (Ia) (0.1 mg/kg)-treated animals.
FIG. 7B is a graphic representation of the change in infarct volume (mm$^3$) at progressive time points during the period of reperfusion following 30 min of ischemia. Each data point (n=4 or 5) represents the mean±SE. *Significant difference (P≤0.05) between vehicle and compound of Formula (Ia) treated rats at the same time point.

In animals pretreated with the compound of Formula (Ia) (0.1 mg/kg) or vehicle and undergoing MCAO for 30 min, a rapid increase in infarct volume from 30 min into the reperfusion period until 2 h of reperfusion was observed (FIG. 7). After 2 h of reperfusion, the mean infarct volume continued to increase significantly in the vehicle group. In contrast to the vehicle-pretreated group, the mean infarct volume in the compound of Formula (Ia) group did not increase further during the remaining reperfusion period (FIG. 7). In addition, the mean infarct volume in the compound of Formula (Ia) group was significantly smaller than the vehicle-pretreated group when measured at 4 and 6 h (P≤0.05 at each time point; FIG. 7). By the end of the 5.5 h of reperfusion, the mean infarct volume of the compound of Formula (Ia) group was ~53% smaller than the vehicle group.

Effect of Compound of Formula (Ia) on SOD Activity.

Figure 8:
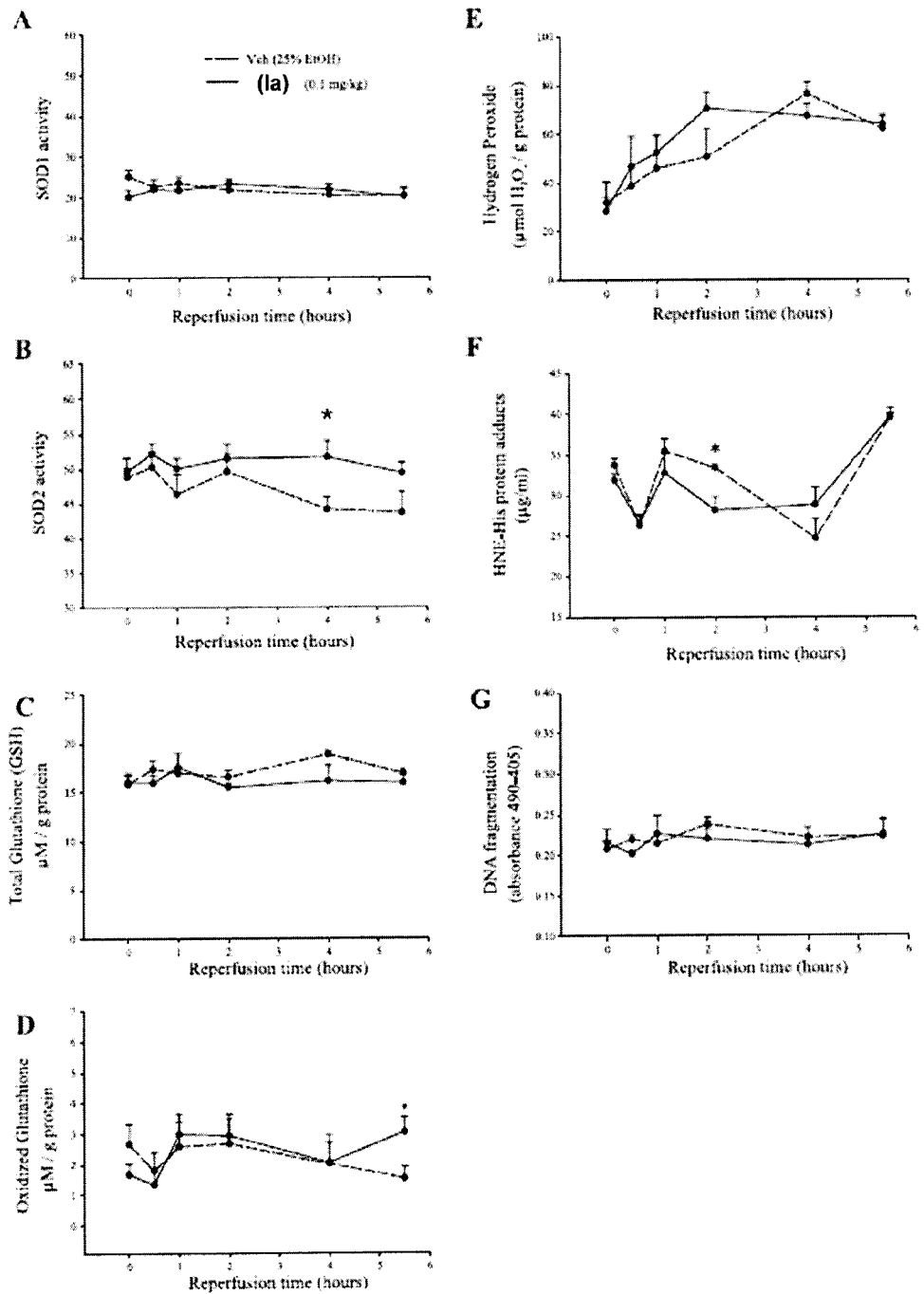
FIG. 8 shows the effect of preadministration (30 min pre-MCAO) of the compound of Formula (Ia) (0.1 mg/kg) or vehicle (25% EtOH) on cytoplasmic copper or zinc superoxide dismutase (Cu/ZnSOD; SOD1) (A) and mitochondrial superoxide dismutase (MnSOD; SOD2) (B) activity (% inhibition of chromogenic reduction); total glutathione (GSH+GSSG) (C) and oxidized glutathione (GSSG) levels (μM/g protein) (0); hydrogen peroxide ($H_2O_2$) levels (μmol $H_2O_2$ per gram of protein) (E); total HNE-His protein adduct levels (μg/ml) (F); the total amount of DNA fragmentation (apoptosis; mean absorption at 405 nm of cytoplasmic nucleosomes) within the infarct area following ischemia/reperfusion (I/R) at progressive time points following the beginning of reperfusion (G). Each data point (n=5/group) represents the mean±SE. *Significant difference (P≤0.05) between vehicle and compound of Formula (Ia)-treated rats at the same time point.

In animals pretreated with compound of Formula (Ia) or vehicle and undergoing MCAO for 30 min, no significant differences in cytoplasmic SOD1 activity levels were observed between these two groups at any time point during 5.5 h of reperfusion (P≥0.05 for each time point measured; FIG. 8A).

In contrast, mitochondrial SOD2 activity levels at the 4-h time point were significantly higher in the compound of Formula (Ia) group compared with vehicle (P≤0.05; FIG. 8B). There were no other significant differences measured at any time point; however, the SOD2 activity levels were consistently higher in the compound of Formula (Ia) group compared with those in the vehicle pretreated group at each time point (FIG. 8B).

Effect of Compound of Formula (Ia) on Glutathione (GSH) Levels.

No significant differences in the total amount of GSH (includes both oxidized and reduced forms) were measured in brain samples taken from either compound of Formula (Ia) or vehicle-treated rats at any time point (P≥0.05 for each comparison; FIG. 8C). In contrast, the amount of the oxidized form of GSH (GSSG) was significantly greater in the compound of Formula (Ia)-treated rats than the amount of GSSG measured in vehicle-treated rats after 5.5 h of reperfusion (P≤0.05; FIG. 8D). There was no difference in the level of GSSG between the two groups at any other time point (P≥0.05 at each time point; FIG. 8D).

Effect of Compound of Formula (Ia) on Hydrogen Peroxide Levels.

In compound of Formula (Ia)-pretreated rats, the level of hydrogen peroxide was not significantly greater than the level of hydrogen peroxide in vehicle-treated rats at any time point over the 5.5 h of reperfusion (P≥0.05; FIG. 8E). However, in both compound of Formula (Ia)—and vehicle-pretreated groups, the level of hydrogen peroxide increased significantly over time (P<0.05; FIG. 8E).

Effect of Compound of Formula (Ia) on Protein (HNE-His) Adduct Levels.

The following experiment was designed to determine whether compound of Formula (Ia)-mediated neuroprotection resulted in a change in HNE-His adduct levels. HNE-His adduct levels following compound of Formula (Ia) administration 30 min prior to occlusion were significantly attenuated compared with vehicle administered following 2 h of reperfusion (P≤0.05; FIG. 8F). HNE-His adduct levels were not significantly different in the two groups at any other time point (P≥0.05 for each time point measured; FIG. 8F).

Effect of Compound of Formula (Ia) on DNA Fragmentation (Apoptotic Cell Death).

The following experiment was designed to determine whether the compound of Formula (Ia)-mediated neuroprotection observed was mediated by an alteration in the extent of apoptotic cell death. DNA fragmentation was quantified as an indicator of apoptotic cell death. No significant changes in the extent of DNA fragmentation in animals pretreated with either the compound of Formula (Ia) or vehicle throughout the experimental time course were observed (P≥0.05 for each time point measured; FIG. 8G).

(c) Discussion

Oxidative stress associated with excessive production of ROS is a fundamental mechanism of brain damage in reperfusion injury following ischemic stroke. The multiplicity of mechanisms involved in ischemia- and reperfusion-induced neuronal damage following an occlusive stroke remains an obstacle in providing treatment in clinical settings.[48] Drugs targeting more than one mechanism of action could potentially overcome this dilemma. The synthesis and development of co-drugs using simple yet biologically relevant molecules as building blocks provide the ability to simultaneously target multiple pathways involved in the pathogenesis of neurological diseases, specifically, pathways involved in the initiation of oxidative stress-induced neuronal damage following reperfusion. Chemical combinations of LA with other compounds have previously done.[74] The inventors are aware of no other reports to date in which apocynin has been chemically linked to other compounds and no other reports to date in which administration of a co-drug was used to attenuate damage due to oxidative stress following ischemia or ischemia/reperfusion.

In the present study, it was determined that the compound of Formula (Ia), a chemical combination of two naturally occurring antioxidants, LA and apocynin, produced dose-dependent neuroprotection against neuronal cell death, as observed in a previously validated, novel model of I/R injury[46]. The results demonstrated that the compound of Formula (Ia) produced dose-dependent, short-term neuroprotection (within 5.5 h of reperfusion) in a model of focal ischemia that is restricted to the cerebral cortex. Further, the dose of the compound of Formula (Ia) required to produce significant neuroprotection (0.1 mg/kg) was many-fold less compared with the doses required for either apocynin[51] or LA[43] on their own. Also, this optimal dose of the compound of Formula (Ia) produced significant neuroprotection when administered 15 min prior to the start of reperfusion, just prior to the induction of reperfusion, and 30, 60, and 90 min following the onset of reperfusion. The reason for administering the compound of Formula (Ia) during the occlusion was to mimic the clinical situation that a patient would present during a stroke. This result does not indicate whether the compound of Formula (Ia) or an intermediate metabolite produced as a result of hepatic biotransformation was responsible for mediating the neuroprotective effect. The dose-dependent neuroprotection was then reproduced with direct cortical injections into the ischemic area, which suggests that the parent compound of Formula (Ia), and not a metabolite(s), was responsible for producing the neuroprotection observed.

There have been other reports that have demonstrated an attenuation of infarct volume when apocynin was administered during an occlusion of the MCA, but these benefits were lost when administration of apocynin was delayed following the onset of reperfusion (Refs. 50-54). However, one laboratory demonstrated that administration of apocynin in gerbils 5 min following 5 min of global ischemia, decreased neuronal degeneration and delayed neuronal death and microglial activation when assessed 4 days later.[55] It is not known whether these apocynin-induced beneficial effects translated to a decrease of infarct size, as it was not measured in that study.

Previous studies have also demonstrated that administration of the most effective dose of LA (5 mg/kg) did not result in significant neuroprotection when administered just prior to the beginning of reperfusion, and only produced neuroprotection when administered prior to both occlusion and reperfusion.[43] Therefore, it appears that the compound of Formula (Ia), a chemical combination of apocynin and LA, is far superior than either compound alone in its ability to provide neuroprotection when administered during reperfusion.

The compound of Formula (Ia) did not produce neuroprotection when administered prior to a 6-h permanent occlusive stroke (no reperfusion). While not wishing to be limited by theory, these results support the suggestion that the compound of Formula (Ia) produced neuroprotection against reperfusion injury alone, perhaps via decreasing ROS production, as ROS-induced growth of ischemic volume due to reperfusion injury has been demonstrated by many laboratories[56], and/or possibly via free radical scavenging.

Clinically, elevated sympathetic tone (sympathoexcitation) and abnormal electrocardiograms have been observed within 1 to 2 h following thrombolytic or hemorrhagic stroke involving the MCA.[57, 58] Such autonomic dysfunction increases the risk of sudden cardiac death[57, 58] and can be mimicked in rat models of MCAO[59]. Arrhythmogenesis and sudden cardiac death, which can occur following MCAO in humans, is associated with depressed baroreflex sensitivity (BRS).[60]

The present results have demonstrated that during the 30-min occlusion, BRS was significantly depressed and administration of the compound of Formula (Ia) did not alter the level of BRS depression despite the compound of Formula (Ia)-induced neuroprotection. The increase in neuronal survival represented by an attenuated ischemic volume was not associated with recovery of autonomic function.

Previous results have demonstrated a similar dissociation between changes in infarct volume and autonomic function following drug intervention prior to MCAO.[61] While not wishing to be limited by theory, it is suggested that for an agent injected systemically, it may be required to have multiple sites of action within the central nervous system, as well as in the periphery (such as the myocardium), to decrease or reverse the sympathoexcitation and subsequent autonomic function observed following stroke. Many studies have demonstrated significant neurochemical and electrophysiological alterations in extracortical autonomic and cardiovascular regulatory nuclei shortly following MCAO.[62] This suggests that any drug that demonstrates functional cardiovascular protection may be required to act extracortically to prevent an abnormal sympathetic outflow and to restore or prevent changes in autonomic function following MCAO.

Neuronal hypoxia and the ensuing mitochondrial response are involved in both the initiation of both necrotic and apoptotic pathways leading to cell death.[63] Severe cerebral ischemia causes neuronal mitochondria to be unable to produce adenosine triphosphate leading to necrotic cell death.[63] The mitochondrial antioxidant enzyme, manganese superoxide dismutase (SOD2) is the primary cellular defense enzyme involved in protecting cells from oxidative stress[63] and has been shown to reduce oxidative stress following cerebral I/R[63], as SOD2-deficient mice have enhanced infarct size following cerebral ischemia[50] and overexpression of SOD2 provided neuroprotection following cerebral ischemia.[50] In the present study enhanced SOD2 activity was observed throughout the 5.5 h of reperfusion (reaching significance following 4 h of reperfusion) when the compound of Formula (Ia) was administered 30 min prior to I/R. It has previously been demonstrated using the same model of I/R that LA administered 30 min prior to I/R also increased SOD2 activity[43], while apocynin was ineffective[51] in altering SOD2 activity.

The compound of Formula (Ia) did not alter cytosolic copper-zinc SOD (CuZnSOD or SOD1) activity, which is consistent with previous results, in which neither of the two parent compounds, apocynin or lipoic acid, altered SOD1 activity.[51, 43] There appears to be support in the literature for a selective effect of LA on mitochondrial function as LA is a protein-bound cofactor for mitochondrial α-ketoacid dehydrogenase and serves a critical role in mitochondrial energy metabolism.[64] In addition, exogenous LA is reduced to dihydro-lipoic acid (DHLA) within the mitochondria[64] and both LA and DHLA have been shown to have powerful antioxidant activity and ROS scavenger abilities.[65] Therefore, it can be concluded that at least part of compound of Formula (Ia)-induced neuroprotection may be due to the actions of the LA functional group of the compound of Formula (Ia) on SOD2 activity.

Glutathione is another key intracellular antioxidant and protects cells by scavenging free radicals (for a review, see ref. 66). Glutathione is involved with the breakdown of peroxides, regulating the nitric acid cycle, DNA synthesis and repair, and maintenance of protein disulfide bonds. In addition to its role in the prevention of oxidative stress, glutathione also helps maintain exogenous antioxidants, such as vitamins C and E. Within cells, glutathione exists as reduced (GSH) and oxidized states (GSSG). In healthy cells, more than 90% of the total glutathione pool is in the reduced form, while less than 10% exists in the oxidized or disulfide form. An increased level of GSSG is generally indicative of enhanced oxidative stress.

It is reported above in the present study that compound of Formula (Ia) administration resulted in a significant increase in the amount of GSSG at the 5.5 h of reperfusion time interval. While not wishing to be limited by theory, it is possible that the compound of Formula (Ia)-induced enhancement in the activity of SOD2 during the 5.5 h of reperfusion resulted in higher levels of hydrogen peroxide production. However, the measured levels of hydrogen peroxide were not different between vehicle and compound of Formula (Ia) groups, indicating that the neurons were able to adequately deal with this excess hydrogen peroxide. Hydrogen peroxide may be fully reduced to water but may also form hydroxyl radicals in the presence of ferrous or cuprous ions.[67] While not wishing to be limited by theory, a slow increase in hydroxyl radical levels over the 5.5 h of reperfusion following compound of Formula (Ia) administration could have attenuated the activity of glutathione reductase, the enzyme responsible for reducing GSSG into GSH, resulting in enhanced levels of GSSG as measured following 5.5 h of reperfusion.

Lipid peroxidation in models of I/R occurs very quickly[68, 55], and byproducts of lipid peroxidation can form adducts with proteins and DNA and, thus, may play an important role in the underlying mechanism for oxidative stress-induced neuronal apoptosis.[69]

The present data suggest that compound of Formula (Ia) pretreatment resulted in a decrease in I/R-induced lipid and protein peroxidation (HNE-His adducts) at 2 h of reperfusion, suggesting that the compound of Formula (Ia) was effective in preventing oxidative stress at this time point. The 2-h time point represents the time when the infarct volume of the compound of Formula (Ia)- and vehicle-treated groups diverges (FIG. 7).

Because the level of apoptotic cell death, measured as the amount of DNA fragmentation, remained the same at all time points during reperfusion, this would suggest that the growth in infarct volume in the vehicle-treated group may have been primarily due to necrotic cell death. While not wishing to be limited by theory, it can be speculated that the increase in neuronal survival measured when rats were pretreated with the compound of Formula (Ia) was due to the ability of the compound of Formula (Ia) to attenuate reperfusion-induced oxidative stress and subsequent necrotic cell death.

Therefore, it can be concluded that during the initial period following stroke and reperfusion, compound of Formula (Ia)-induced neuroprotection was primarily due to increased SOD2 activity, thereby causing an increase in the neurons' ability to immediately deal with reperfusion-induced mitochondrial superoxide production. This, along with reduced peroxidation of lipids and proteins as a result of oxidative stress, combined to produce the observed neuroprotective capacity of the compound of Formula (Ia).

It should be mentioned that although time-dependent measures of molecular mediators of cellular stress pathways were conducted, these changes do not necessarily suggest a cause-and-effect relationship between the compound of Formula (Ia) and these proteins. This is particularly true since the temporal changes in these proteins do not correspond to all time points in which neuroprotection was observed. This is studied utilizing siRNA technology so as to establish this relationship.

At present, there are no pharmacological treatments available other than thrombolytic therapy, such as tissue plasminogen activator (tPA), and this is used in only about 4% of patients presenting to a hospital following an acute ischemic stroke.[70] In addition, patients must present themselves to a hospital within ~4 h of the stroke onset to be eligible for tPA therapy.[71] Providing effective pharmacological treatment immediately following an acute stroke to lessen the cerebral damage has been an elusive goal. The compound of Formula (Ia) is a potential therapeutic candidate to protect against the negative outcomes associated with reperfusion-induced ischemia.

Example 8

Stability of the Compound of Formula (Ia) in Buffer

Figure 9:
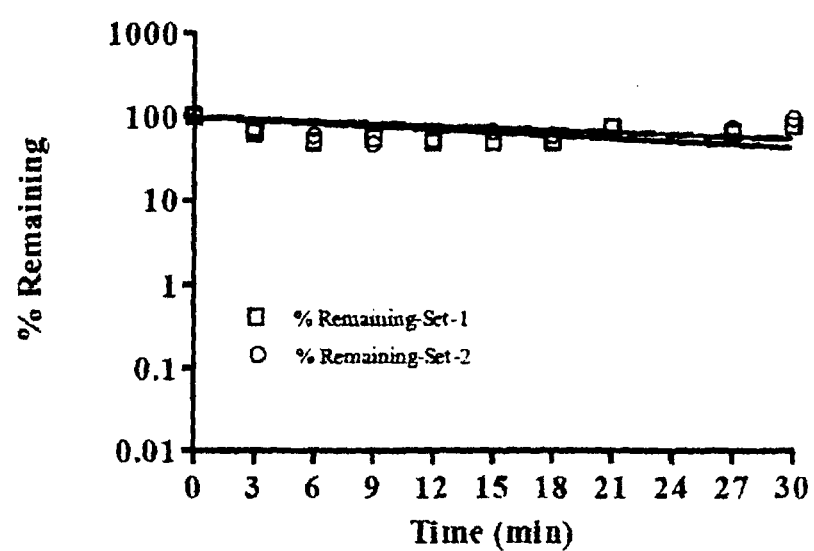
FIG. 9 shows the stability of the compound of Formula (Ia) at a concentration of 0.5 μM in sodium phosphate buffer (50 mM, pH 7.4). The percentage remaining is calculated based on the Area ratio.
Figure 10:
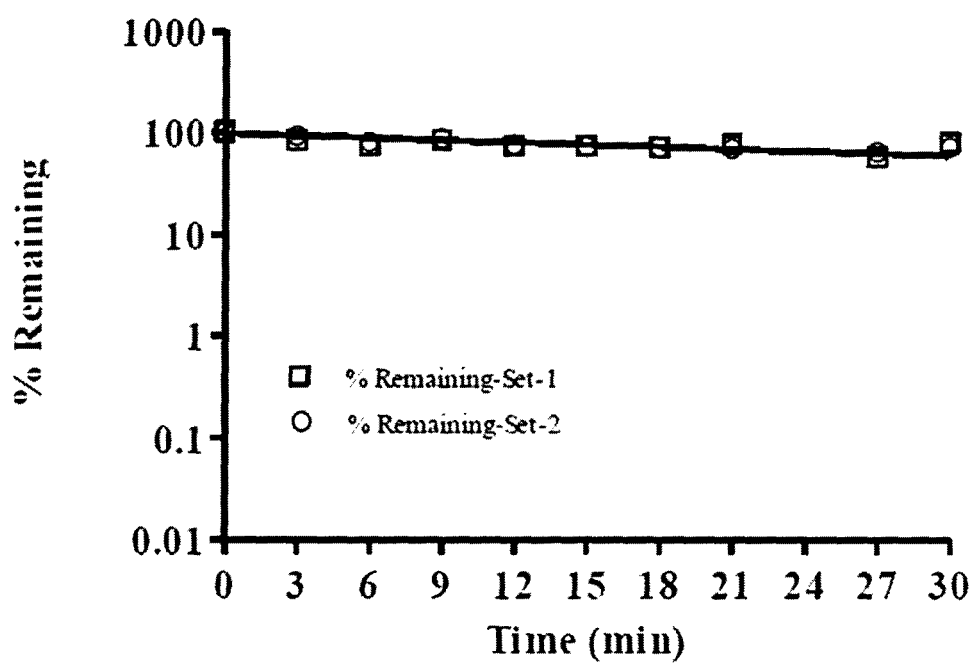
FIG. 10 shows the stability of the compound of Formula (Ia) at a concentration of 10 μM in sodium phosphate buffer (50 mM, pH 7.4). The percentage remaining is calculated based on the Area ratio.
Figure 11:
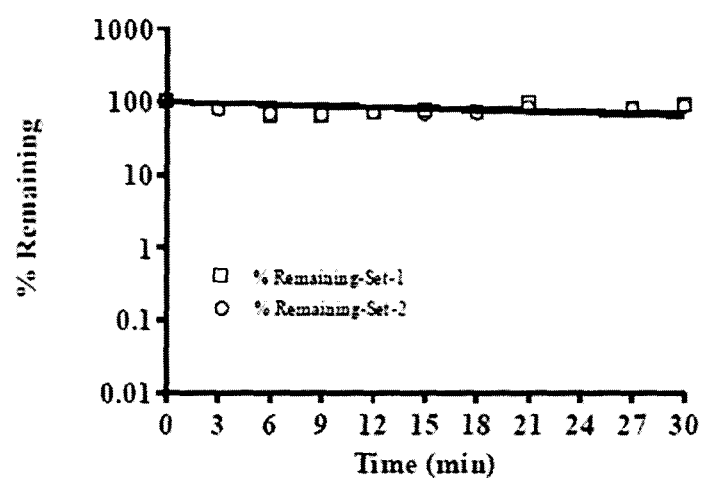
FIG. 11A shows the apocynin area counts in samples spiked with the compound of Formula (Ia) at a concentration of 0.5 μM.
FIG. 11B shows the apocynin area counts in samples spiked with the compound of Formula (Ia) at a concentration of 10 μM.
Figure 11:
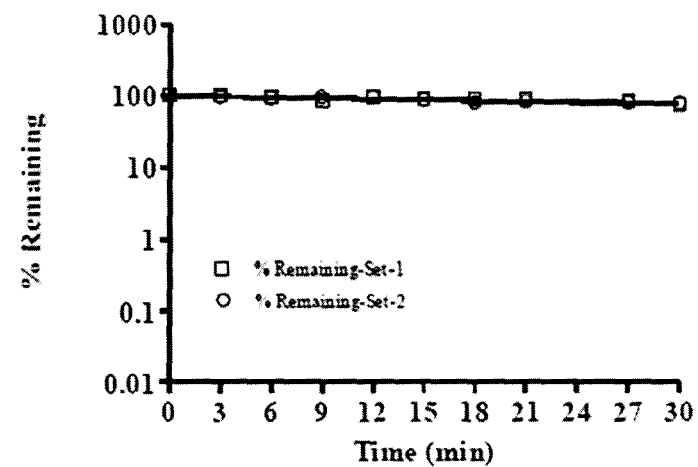
Figure 12:
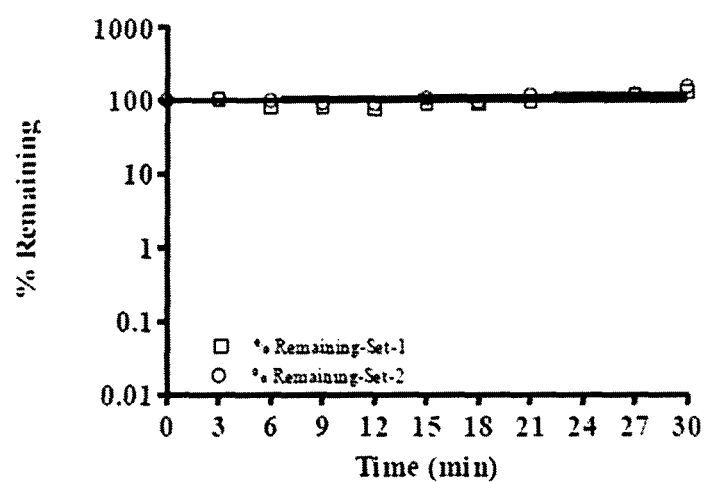
FIG. 12A shows the lipoic acid area counts in samples spiked with the compound of Formula (Ia) at a concentration of 0.5 μM.
FIG. 12B shows the lipoic acid area counts in samples spiked with the compound of Formula (Ia) at a concentration of 10 μM.
Figure 12:
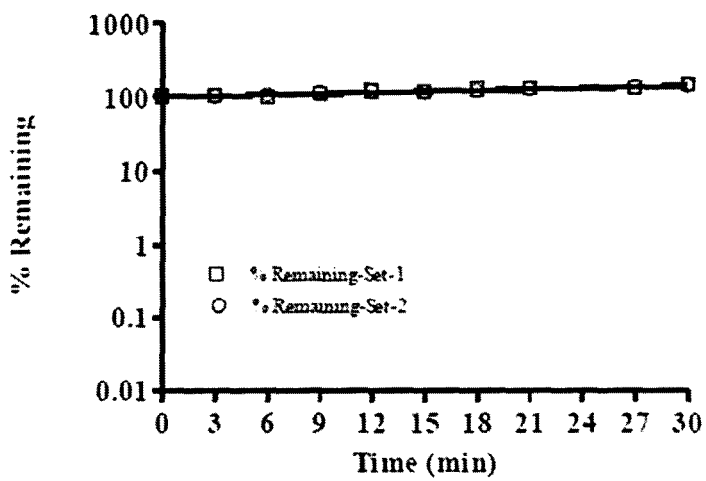

The stability of the compound of Formula (Ia) in a sodium phosphate buffer (50 mM, pH 7.4) was evaluated using HPLC. The compound of Formula (Ia) was found to be stable in the sodium phosphate buffer at concentrations of 0.5 µM and 10 µM (see: FIGS. 9-10 and Tables 3-4). Area counts of apocynin and lipoid acid were found in 0 minute samples and were generally constant until the last time point measured (see: FIGS. 11-12 and Tables 5-6).

Example 9

Metabolic Stability Assessment of the Compound of Formula (Ia): Studies in Human, Dog, and Liver Microsomes (a) Summary Screening for lead compound breakdown by the hepatocytes (the primary cell type of the liver) is a simple and effective method to measure potential biologically relevant metabolic vulnerability to drug metabolizing enzymes. This process is enhanced in studying several animal species. For the compound of Formula (Ia), microsomal assays were performed in human, dog, and rat liver.

The HPLC method for the analysis of test item in dose formulation samples was validated by assessment of the specificity, linearity and range, precision and accuracy and intermediate precision of the assay method as described in greater detail below. The stability of working standard and sample solutions under specified storage conditions was also assessed as described in greater detail below.

Figure 13:
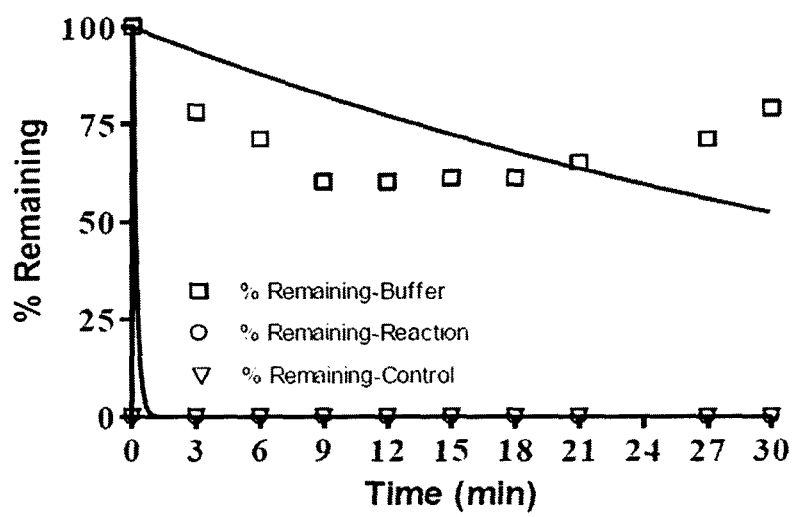
FIG. 13 shows the results from studies of the metabolic stability of the compound of Formula (Ia) using rat liver microsomes.
Figure 13:
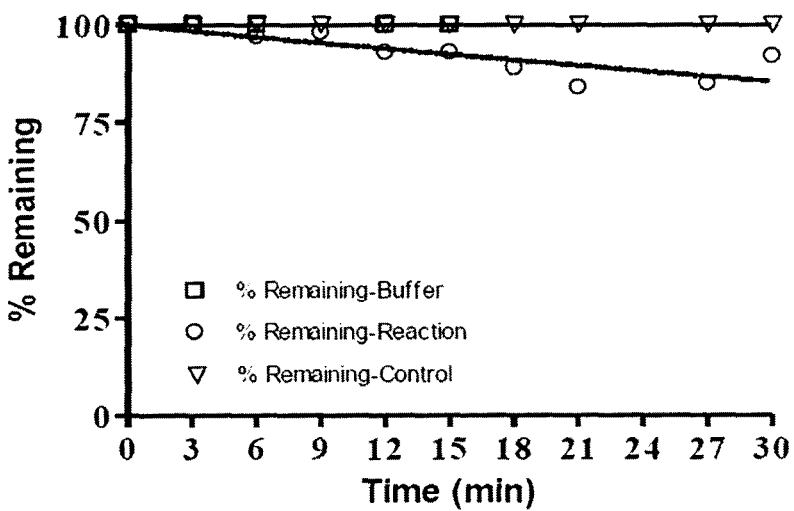
Figure 13:
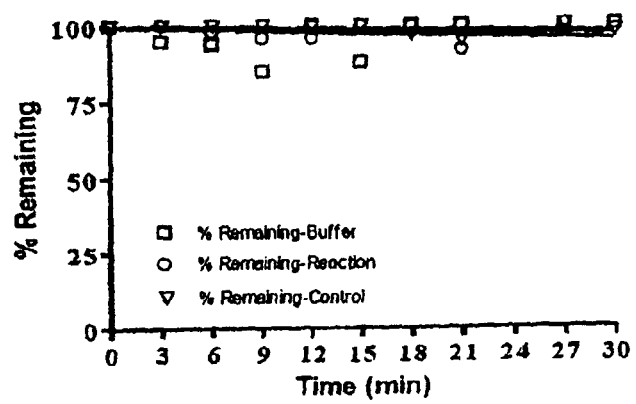
Figure 13:
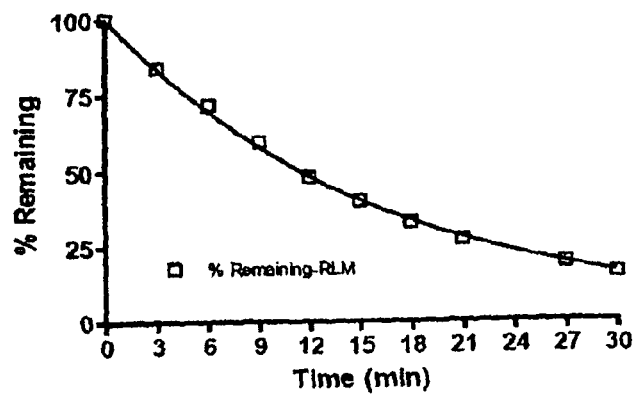

Table 7 summarizes the experimental conditions used in the studies of the metabolic stability of the compound of Formula (Ia) using rat liver microsomes. Table 8 and FIG. 13 show the results from the studies of the metabolic stability of the compound of Formula (Ia) using rat liver microsomes.

Figure 14:
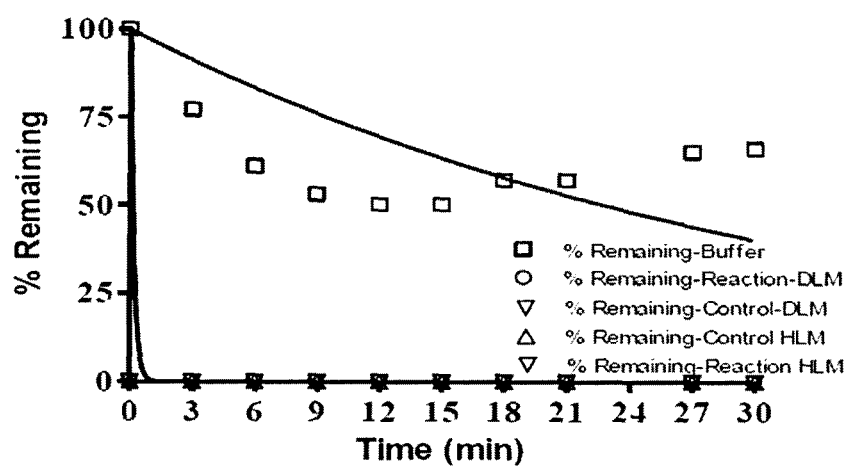
FIG. 14 shows the results from studies of the metabolic stability of the compound of Formula (Ia) using dog liver microsomes (DLM) and human liver microsomes (HLM).
Figure 14:
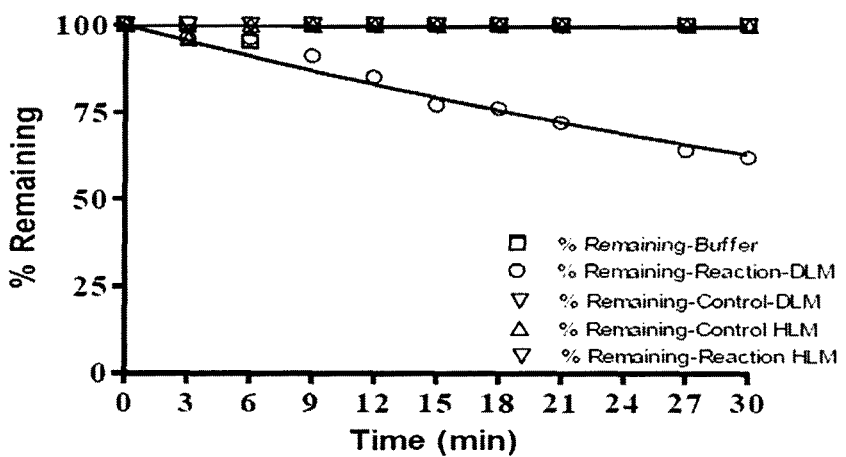
Figure 14:
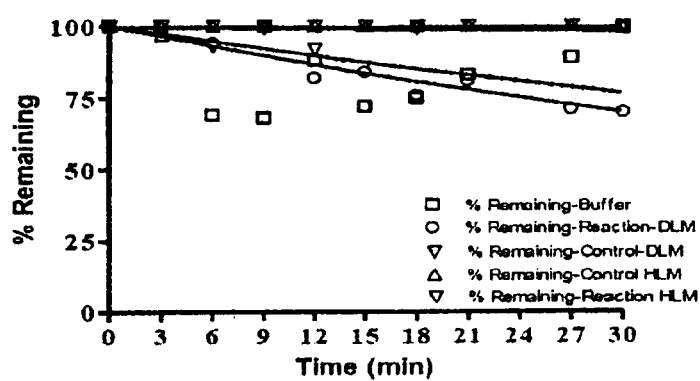
Figure 14:
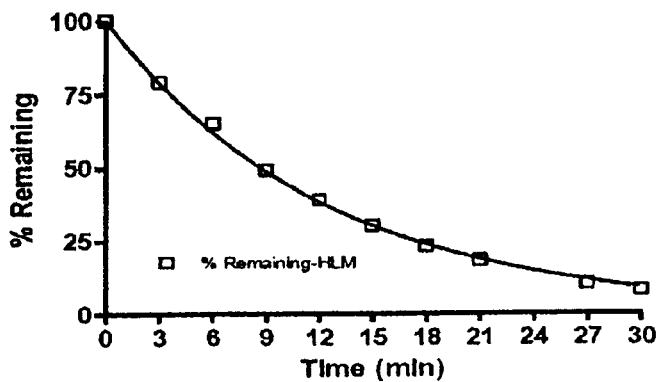
Figure 14:
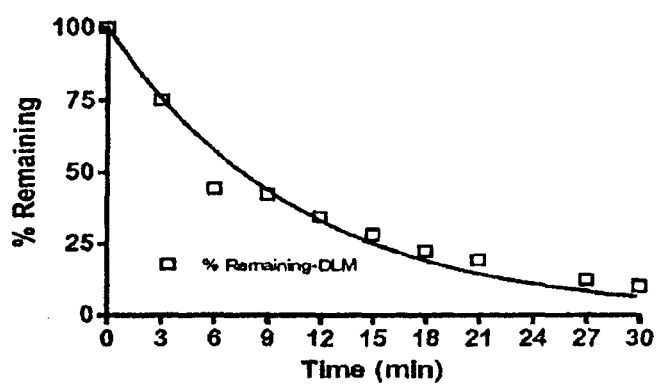

Table 9 summarizes the experimental conditions used in the studies of the metabolic stability of the compound of Formula (Ia) using dog liver microsomes and human liver microsomes. Table 10 and FIG. 14 show the results from the studies of the metabolic stability of the compound of Formula (Ia) using dog liver microsomes (DLM) and human liver microsomes (HLM).

Utilizing diclofenac and verapamil as positive controls, it was determined that the compound of Formula (Ia) indicated metabolic stability and one phase exponential delay in all three species. There was no evidence of increasing concentrations of the compound of Formula (Ia) in any time-course microsomal assays, suggesting that the compound of Formula (Ia) is rapidly cleared by the liver and does not cause an increased risk of toxicity.

(b) Validation of the Analytical Method
Experimental Design

The High Performance Liquid Chromatograph (HPLC) method for the analysis of the test item in dose formulation samples was validated by assessment of the specificity, linearity and range, precision and accuracy, and intermediate precision of the assay method. The stability of the working standard and sample solutions under specified storage conditions was assessed.

Specificity

A blank of diluent and vehicle (after processing as per the method being validated) was injected into an HPLC and the absence of an interference peak at the retention time of the compound of Formula (Ia) was confirmed to ensure specificity of the method.

Linearity and Range

For detector linearity, a minimum of five standard solutions ranging at least from 50% to 150% of the test concentration of the analyte was injected into the HPLC in triplicate. A graph of detector response versus concentration was plotted (concentration on X-axis and detector response on Y-axis) and correlation coefficient (r) was established.

Accuracy and Precision

Test item concentrations in the dose formulations at two dose levels (low and high in vehicle) was analyzed in at least six replicates (at least 2 replicates from the top, middle layer and bottom layers) using the method being validated. Accuracy as percent recovery was calculated for each analyte.

Intermediate Precision

The intermediate precision of the method was demonstrated by using a different HPLC system and the test carried out by a different analyst on the dosing formulations of the test item in at least six replicates (at least 2 replicates from the top, middle layer and bottom layers) of each of the test concentrations on a different day.

The test item was analyzed using the method being validated. Precision of the method was acceptable if composite % RSD of assay from at least twelve replicates (at least six replicates of precision and at least six replicates of intermediate precision) for each dose level were less than 10%.

Solution (Injection Medium) Stability

Stability of prepared analytical solutions was established by re-injection (in triplicate) of the standard solution and two sample solutions (of precision or of intermediate precision test), one corresponding to low dose and the other corresponding to high dose along with a freshly prepared standard solution (bracketing). The obtained concentrations were compared to the original concentration of the precision/intermediate precision test results.

The stability was evaluated for the solutions stored at ambient temperature after at least 24 and 48 h. The solutions were considered stable if the results were within ±10% of the original value.

(c) Homogeneity, Re-Suspendability and Stability Tests
Experimental Design

Homogeneity, re-suspendability and stability of test item in the vehicle was performed at 0.1 mg/mL (low dose) and 100 mg/mL (high dose) concentration levels.

Homogeneity

For the homogeneity test, the following samples were collected: One sample from vehicle and at least six replicates (at least 2 replicates from the top, middle layer and bottom layers) for each dose group (low and high) were drawn and analyzed for the test item concentration.

The homogeneity of the formulations were considered acceptable if the mean results were within ±15% of the mean concentration and the mean relative standard deviations (% RSD) equal to or less than 10%.

Re-Suspendability and Stability

The dose formulations, after sampling for the homogeneity test were stored at room temperature for at least 8 days. Also, a portion of the formulation was sampled at 0 hour/day and stored at refrigerated conditions (+2 to +8° C.) for at least 8 days.

Samples were drawn for analysis at the following intervals:
0 hour (Overall mean concentration obtained for homogeneity test was used as concentration at '0' hour)
4 hours (samples stored at room temperature)
24 hours (samples stored at room temperature)
4 days (samples stored at room temperature)
8 days [samples stored at room temperature and at refrigerated conditions (+2 to +8° C.)]

For analysis at each occasion, samples were stirred on a magnetic stirrer for at least 15 min. before sampling.

At least six replicates (at least 2 replicates from the top, middle layer and bottom layers) for each dose group (low and high) were drawn and analyzed for the test item concentrations.

Example 10

Bioanalytical Method Development for Quantification of the Compound of Formula (Ia) in Plasma (a) Introduction and Overview As described below, during development, the compound of Formula (Ia) was found to be unstable in biological matrices. While not wishing to be limited by theory, ester bond hydrolysis is a potential reason for this.

Figure 15:
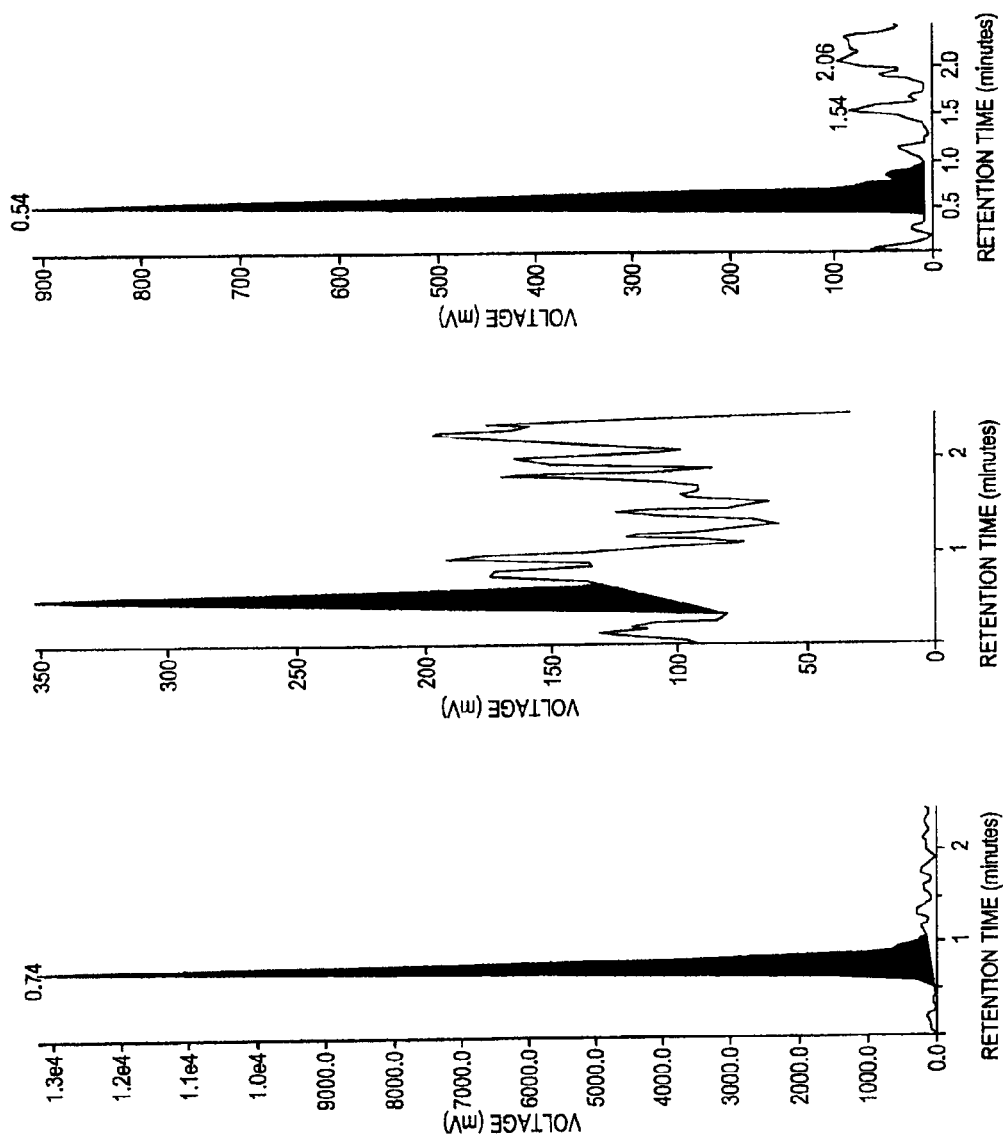
FIG. 15 shows a chromatogram of a neat sample of the compound of Formula (Ia) showing the presence of the compound of Formula (Ia), and little traces of apocynin and lipoic acid (left). Chomatograms of apocynin (center) and lipoic acid (right) are shown for comparative purposes.
Figure 16:
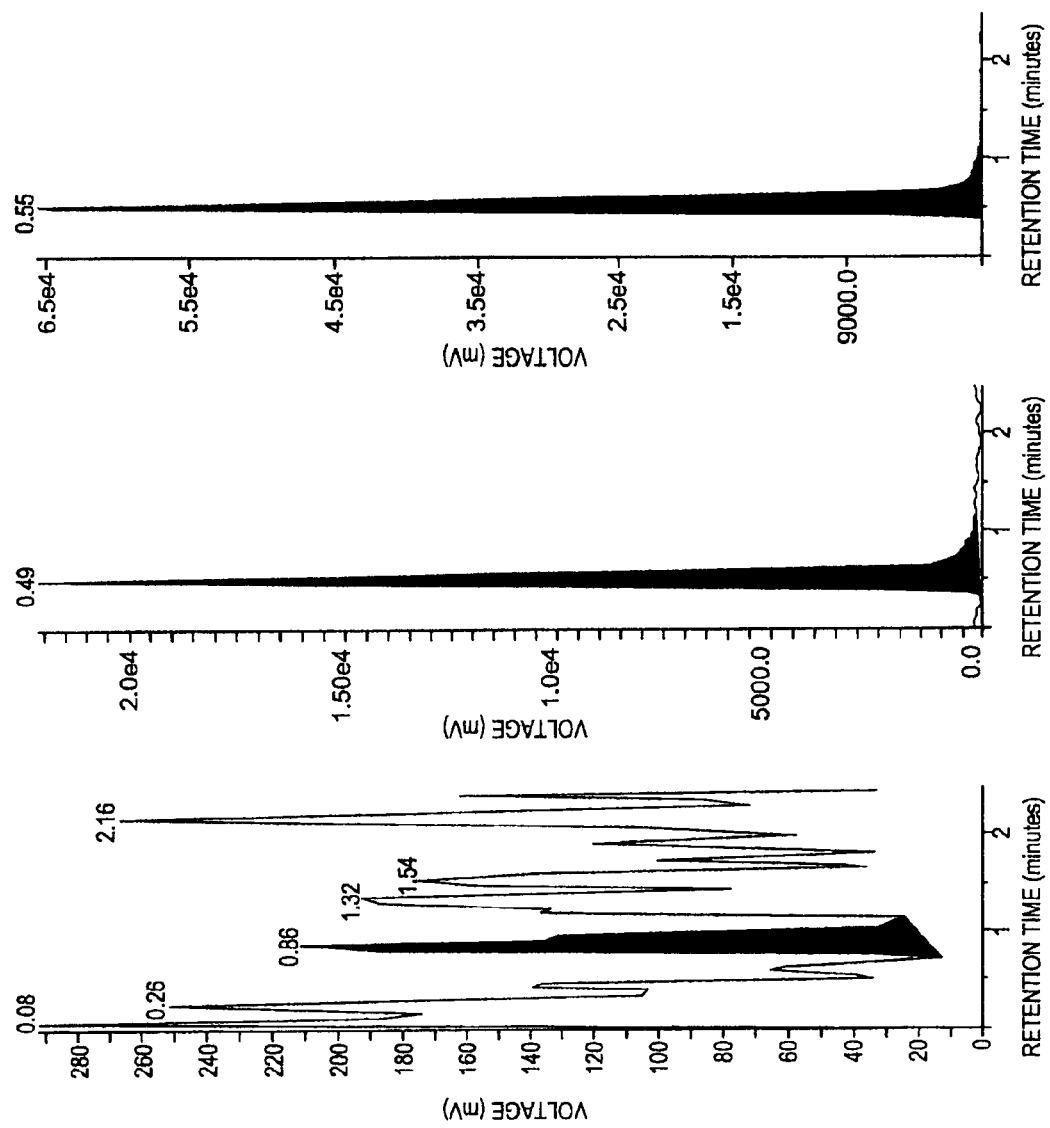
FIG. 16 shows a chromatogram of a compound of Formula (Ia) spiked plasma sample (immediate extraction) showing a minor trace of the compound of Formula (Ia) (nearly 0% remaining), and a significant presence of apocynin and lipoic acid (left). Chomatograms of apocynin (center) and lipoic acid (right) are shown for comparative purposes.

The compound of Formula (Ia) was found to disappear upon fresh spiking and extraction from plasma. Apocynin and Lipoic acid (LA) was found to appear in compound of Formula (Ia)-spiked samples (See chromatogram at the left of FIG. 16, compared to the chromatogram at the left of FIG. 15).

Figure 17:
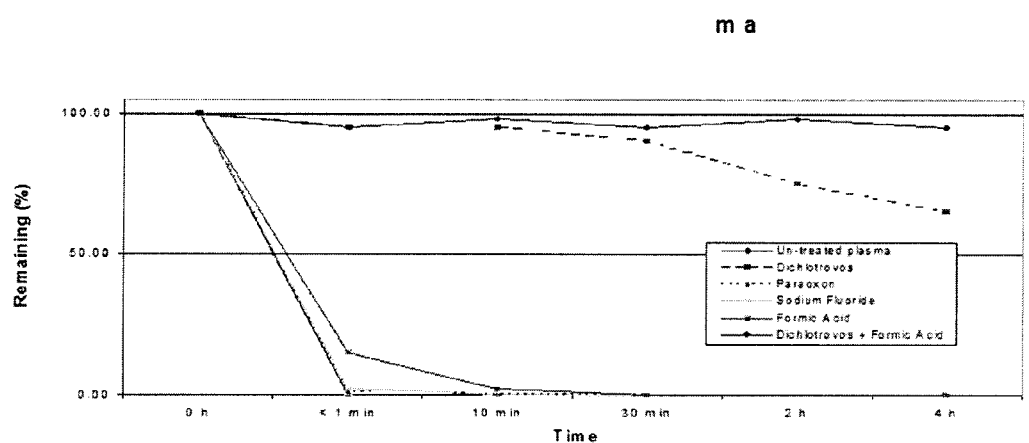
FIG. 17 shows the stability of the compound of Formula (Ia) in plasma in the presence of various compounds. The compound of Formula (Ia) could be stabilized for about 4 hours at ambient conditions using a combination of the esterase inhibitors diclorvos and formic acid.

The compound of Formula (Ia) could be stabilized for about 4 hours at ambient conditions by using a combination of the esterase inhibitors dichlorvos and formic acid (see FIG. 17 and Table 11).

Stabilization for the compound of Formula (Ia) in biological matrices (especially blood) is a challenge; a lag time of seconds prior to stabilizer additions would result in analyte concentration manipulation. Attempts to date to stabilize the compound of Formula (Ia) in whole blood have been unsuccessful, leading to sample homogeneity issues.

(b) Bioanalytical Development

The compound of Formula (Ia) stock (1 mg/mL) was prepared in methanol because the compound of Formula (Ia) was found to be stable in methanolic solution.

Method Development

Tuning for mass spectrometry was performed: Positive/Negative mode ionization (ESI): Compound of Formula (Ia): Q1/355.2, Q3/161.1 and 189.2; Apocynin: Q1/165.1, Q3/149.9; Lipoic acid: Q1/204.7, Q3/170.9.

Initial suitable chromatographic conditions were achieved.

Extraction Trials

Extraction of the compound of Formula (Ia) from rat plasma was attempted. No recovery was observed with LLE (liquid-liquid extraction) using MTBE (methyl t-butyl ether). Similar results were observed with PPT (protein precipitation) using acetonitrile and methanol.

It was identified that the compound of Formula (Ia) was not stable in biological matrix.

Stabilizing the Compound of Formula (Ia) in Plasma

Various esterase inhibitors, for example, Paraoxon ethyl, Dichlorvos (DV), Sodium fluoride, HCl, formic acid (FA), etc. were evaluated. See FIG. 17 and Table 11 for the results of such studies.

Dichlorvos was found to be suitable to stabilize the compound of Formula (Ia) in plasma for up to 2 h. A combination of DV and FA was found to stabilize the compound of Formula (Ia) in plasma for up to 4 h. Some precipitate was observed because of the formic acid.

Stability was assessed at different concentrations of analyte and at different concentrations of DV and FA.

Stabilizing the compound of Formula (Ia) in whole blood is a challenge which may, for example, lead to disruption of sample homogeneity (c) Summary and Further Comments The compound of Formula (Ia) was observed to be stable in methanolic solutions and in buffer at pH 7.4, but it was observed to be unstable in biological matrix, rat/dog blood and plasma. Stabilizing blood affects the nature of the sample (for example, clot/lump formation and/or different degree of hemolysis etc.) which may lead to sample homogeneity issues. This is not a recommended scenario for regulatory studies and could lead to non-reproducibility issues. Considering the instability of the compound of Formula (Ia), for toxicokinetic evaluation studies, the quantification of LA and apocynin is a preferred option. However, endogenous levels of LA during development should be considered. The significance of this data is uncertain considering the compounds of Formula (Ia) was shown to have significantly improved activity in vivo compared to apocynin and LA on its own. Clearly there is something further underlying the compound's activity.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Effects of (Ia) and NADPH oxidase inhibitors on DNA cell fragmentation*

| | |
|---|---|
| Control | 100 |
| Hydrogen Peroxide (6 hr) | 428 ± 52 |
| Apocynin | 244 ± 32** |
| DPI | 208 ± 38** |
| (Ia) | 138 ± 20**# |

*n = 4 for each group; values are percentage of control

**value differs ($p < 0.05$) from hydrogen peroxide value differs ($p < 0.05$) from apocynin and DPI

TABLE 2

SAMP-8 Mouse Model
Table 2: SAMP-8 mouse model

| | |
|---|---|
| Age of Procurement (4 weeks for both models) | Animals allowed to acclimatize for 2 weeks<br>Treatment Begins at 5 weeks |
| Groups | Randomized to 3 groups: Control (10), Low Dose compound of Formula (Ia) (10), High Dose compound of Formula (Ia) (10). Dosage will be determined based on Ki testing. |
| N, number of animals | 30 animals total (10 per group) |
| Diet and Water | Control lab chow (10 kcal % Fat)<br>1% NaCl containing water |
| Route/Dose * of Administration | Orally administered by gavage feeding |
| End-points for specific aims | 4 weeks<br>1. Weight and Blood pressure (tail cuff) every week<br>2. Endothelial Function [Acetylcholine (Ach) and Sodium nitroprusside, (SNP)], and constrictor responses to phenylephrine in brain and thoracic aorta<br>3. RT-PCR for neuronal and myocardial gene expression of hsp70 and hsp90<br>4. Immunohistochemistry for macrophage (F4/80) infiltration in brain and heart, Nitrotyrosine residues by western and IHC<br>5. Superoxide generation in the brain and heart;<br>6. Plasma markers of inflammation: IL-6, CRP, TNF, Isoprostanes, VCAM-1, MCP-1, ICAM-1<br>7. Immunoblots for endothelial nitric oxide synthase (eNOS), neuronal NOS (nNOS) and phospho-eNOS expression; Akt and phospho-Akt expression.<br>8 weeks<br>Mortality and morbidity events (Kaplan Meier) |

* performed at baseline and exit

TABLE 3

Stability of compound of Formula (Ia) in buffer at 0.5 μM

| | % Remaining | |
|---|---|---|
| Time (Min) | Set-1 | Set-2 |
| 0 | 100 | 100 |
| 3 | 64 | 71 |
| 6 | 50 | 59 |
| 9 | 55 | 47 |
| 12 | 50 | 53 |
| 15 | 50 | 65 |
| 18 | 50 | 59 |
| 21 | 73 | 76 |
| 27 | 64 | 71 |
| 30 | 77 | 94 |

TABLE 4

Stability of compound of Formula (Ia) in buffer at 10 μM

| | % Remaining | |
|---|---|---|
| Time (Min) | Set-1 | Set-2 |
| 0 | 100 | 100 |
| 3 | 83 | 92 |
| 6 | 73 | 80 |
| 9 | 83 | 87 |
| 12 | 73 | 76 |
| 15 | 74 | 72 |
| 18 | 71 | 71 |
| 21 | 76 | 69 |
| 27 | 57 | 64 |
| 30 | 79 | 71 |

TABLE 5

Apocynin area counts in samples spiked with the compound of Formula (Ia) at concentrations of 0.5 μM and 10 μM

| | Apocynin (compound of Formula (Ia); 0.5 μM) % Remaining | | Apocynin (compound of Formula (Ia); 10 μM) % Remaining | |
|---|---|---|---|---|
| Time (Min) | Set-1 | Set-2 | Set-1 | Set-2 |
| 0 | 100 | 100 | 100 | 100 |
| 3 | 81 | 78 | 100 | 96 |
| 6 | 66 | 68 | 94 | 91 |
| 9 | 62 | 65 | 85 | 94 |
| 12 | 72 | 71 | 97 | 95 |
| 15 | 76 | 68 | 90 | 86 |
| 18 | 72 | 70 | 90 | 80 |
| 21 | 93 | 82 | 88 | 82 |
| 27 | 79 | 79 | 82 | 80 |
| 30 | 89 | 85 | 73 | 78 |

TABLE 6

Lipoic acid area counts in samples spiked with the compound of Formula (Ia) at concentrations of 0.5 μM and 10 μM

| | Lipoic acid (compound of Formula (Ia); 0.5 μM) % Remaining | | Lipoic acid (compound of Formula (Ia); 10 μM) % Remaining | |
|---|---|---|---|---|
| Time (Min) | Set-1 | Set-2 | Set-1 | Set-2 |
| 0 | — | 100 | 100 | 100 |
| 3 | 100 | 103 | 101 | 100 |
| 6 | 79 | 99 | 98 | 105 |
| 9 | 79 | 91 | 111 | 113 |
| 12 | 75 | 89 | 119 | 118 |
| 15 | 92 | 106 | 115 | 114 |
| 18 | 92 | 96 | 126 | 121 |
| 21 | 96 | 117 | 131 | 127 |
| 27 | 113 | 119 | 133 | 134 |
| 30 | 128 | 151 | 149 | 141 |

TABLE 7

Metabolic stability of the compound of Formula (Ia) using rat liver microsomes (experimental conditions used in the studies).

| | Buffer | Reaction (with NADPH) | Control (without NADPH) |
|---|---|---|---|
| NADPH (20 mM) (μL) | — | 100 | — |
| Microsomes (μL) | — | 25 | 25 |
| Test item (100 μM, methanol) (μL) | 5 | 5 | 5 |
| Sodium phosphate buffer (50 mM, pH 7.4) (μL) | 995 | 870 | 970 |
| Total volume (μL) | 1000 | 1000 | 1000 |
| Number of experiments | 1 | 1 | 1 |

Final organic content in the reaction mix: 0.5% methanol
Sampling time points (buffer, control, reaction): 0, 3, 6, 9, 12, 15, 18, 21, 27 and 30 minutes
Sampling volume: 50 μL
Quenching solvent and volume: methanol, 50 μL

TABLE 8

Metabolic stability of the compound of Formula (Ia) using rat liver microsomes (RLM) (results).

| Compound | Matrix | % Metabolism in 30 minutes | Half life (min) | $CL_{intr}$ (mL/min/g liver) |
|---|---|---|---|---|
| compound of Formula (Ia) | buffer | 21 | >30 | 2.3 |
| | control | 0 | 0 | >67 |
| | reaction | 0 | 0 | >67 |
| apocynin | buffer | 0 | >30 | <0.6 |
| | control | 2 | >30 | <0.6 |
| | reaction | 0 | >30 | <0.6 |
| lipoic acid | buffer | 0 | >30 | <0.6 |
| | control | 0 | >30 | <0.6 |
| | reaction | 8 | >30 | <0.6 |
| diclofenac | RLM | 84 | 11 | 6.4 |

TABLE 9

Metabolic stability of the compound of Formula (Ia) using dog liver microsomes (DLM) and human liver microsomes (HLM) (experimental conditions used in the studies).

| | Buffer | Reaction (with NADPH) | Control (without NADPH) |
|---|---|---|---|
| NADPH (20 mM) (μL) | — | 100 | — |
| Microsomes (μL) | — | 25 | 25 |
| Test item (100 μM, methanol) (μL) | 5 | 5 | 5 |

TABLE 9-continued

Metabolic stability of the compound of Formula (Ia) using dog liver microsomes (DLM) and human liver microsomes (HLM) (experimental conditions used in the studies).

| | Buffer | Reaction (with NADPH) | Control (without NADPH) |
|---|---|---|---|
| Sodium phosphate buffer (50 mM, pH 7.4) (μL) | 995 | 870 | 970 |
| Total volume (μL) | 1000 | 1000 | 1000 |
| Number of experiments | 1 | 1 | 1 |

Final organic content in the reaction mix: 0.5% methanol
Sampling time points (buffer, control, reaction): 0, 3, 6, 9, 12, 15, 18, 21, 27 and 30 minutes
Sampling volume: 50 μL
Quenching solvent and volume: methanol, 50 μL

TABLE 10

Metabolic stability of the compound of Formula (Ia) using dog liver microsomes (DLM) and human liver microsomes (HLM) (results).

| Compound | Matrix | % Metabolism in 30 minutes | Half life (min) | $CL_{int}$ (mL/min/g liver) |
|---|---|---|---|---|
| compound of Formula (Ia) | buffer | 34 | 23 | 3.2 |
| | DLM control | 0 | 0 | >67 |
| | DLM reaction | 0 | 0 | >67 |
| | HLM control | 0 | 0 | >67 |
| | HLM reaction | 0 | 0 | >67 |
| lipoic acid | buffer | 0 | >30 | 0.9 |
| | DLM control | 0 | >30 | <0.6 |
| | DLM reaction | 38 | >30 | 1.2 |
| | HLM control | 0 | >30 | <0.6 |
| | HLM reaction | 0 | >30 | <0.6 |
| apocynin | buffer | 1 | >30 | <0.6 |
| | DLM control | 0 | >30 | <0.6 |
| | DLM reaction | 30 | >30 | 1.6 |
| | HLM control | 0 | >30 | <0.6 |
| | HLM reaction | 0 | >30 | <0.6 |
| verapamil | DLM | 90 | 8 | 9.7 |
| diclofenac | HLM | 92 | 9 | 8.4 |

TABLE 11

Stability of the compound of Formula (Ia) in plasma in the presence of various stabilizers

| | % Change with time | | | | | |
|---|---|---|---|---|---|---|
| Stabilizer | 0 h | <1 min | 10 min | 30 min | 2 h | 4 h |
| Un-treated plasma | 100.00 | 0.00 | — | — | — | — |
| Formic acid | 100.00 | 15.00 | 2.00 | — | — | — |
| Sodium fluoride | 100.00 | 2.00 | — | — | — | — |
| Paraoxon | 100.00 | 1.00 | — | — | — | — |
| Dichlorvos | 100.00 | 95.00 | 95.00 | 90.00 | 75.00 | 65.00 |
| Dichlorvos + Formic acid | 100.00 | 95.00 | 98.00 | 95.00 | 98.00 | 95.00 |

FULL CITATIONS FOR DOCUMENTS REFERRED TO IN THE SPECIFICATION

1. Halliwell, B. Reactive oxygen species and the central nervous system. J Neurochem 59, 1609-1623 (1992).
2. Kontos, H. A. Oxygen radicals in CNS damage. Chemico-Biological Interactions 72, 229-255 (1989).
3. Tieu, K., Ischiropoulos, H. & Przedborski, S. Nitric oxide and reactive oxygen species in Parkinson's disease. IUBMB Life 55 (2003).
4. Yokoyama, H., Takagi, S., Watanabe, Y., Kato, H. & Araki, T. Role of reactive nitrogen and reactive oxygen species against MPTP neurotoxicity in mice. Neural Transm 115, 831-842 (2008).
5. Datla, S. R. & Griendling, K. K. Reactive oxygen species, NADPH oxidase, and hypertension. Hypertension 56, 325-330 (2010).
6. NCHS, Centers for Disease Control. Summary Health Statistics for US Adults. (2007).
7. Babior, B. M. NADPH oxidase. Curr Opin Immunol 16, 42-47 (2004).
8. Zhang, R. et al. Isoforms and Functions of NAD(P)H Oxidase at the Macula Densa. Hypertension 53, 556-563 (2009).
9. Holland, J. A., O'Donnell, R. W., Chang, M. M., Johnson, D. K. & Ziegler, L. M. Endothelial cell oxidant production: Effect of NADPH oxidase inhibitors. Endothelium 7, 109-119 (1999).
10. Hamilton, C. A., Brosnan, M. J., Al-Benna, S., Berg, G. & Dominiczak, A. F. NAD(P)H oxidase inhibition improves endothelial function in rat and human blood vessels. Hypertension 40, 755-762 (2002).
11. Brandes, R. P. A radical approach: the quest for specific functions and inhibitors of vascular NADPH oxidase. Circ Res 92, 583-585 (2003).
12. Guzik, T. J. & Harrison, D. G. Vascular NADPH oxidases as drug targets for novel antioxidant strategies. Drug Discov Today 11, 524-533 (2006).
13. Stolk, J., Hiltermann, T. J., Dijkman, J. H. & Verhoeven, A. J. Characteristics of the inhibition of NADPH oxidase activation in neutrophils by apocynin, a methoxy-substituted catechol. Am J Respir Cell Mol Biol 11, 95-102 (1994).
14. Barbieri, S. S. et al. Apocynin prevents cyclooxygenase 2 expression in human monocytes through NADPH oxidase and glutathione redox-dependent mechanisms. Free Radic Biol Med 37, 156-165 (2004).
15. Ellis, J. A., Mayer, S. J. & Jones, O. T. The effect of the NADPH oxidase inhibitor diphenyleneiodonium on aerobic and anaerobic microbicidal activities of human neutrophils. Biochem J 251, 887-891 (1988).
16. Simons, J. M., Hart, B. A., Ip Vai Ching, T. R., Van, D. H. & Labadie, R. P. Metabolic activation of natural phenols into selective oxidative burst agonists by activated human neutrophils. Free Radic Biol Med 8 251-258 (1990).
17. Engels, F., Renirie, B. F., Hart, B. A., Labadie, R. P. & Nijkamp, F. P. Effects of apocynin, a drug isolated from the roots of *Picrorhiza kurroa*, on arachidonic acid metabolism. FEBS Lett 305, 254-256 (1992).
18. Olas, B., Wachowicz, B., Stochmal, A. & Oleszek, W. Inhibition of oxidative stress in blood platelets by different phenolics from *Yucca schidigera* Roezl. bark. Nutrition 19, 633-640 (2003).
19. Ungvari, Z. et al. Resveratrol increases vascular oxidative stress resistance. Am J Physiol 292, H2417-H2424 (2007).
20. Thatte, U., Bagadey, S. & Dahanukar, S. Modulation of programmed cell death by medicinal plants [Review]. Cell Mol Biol 46, 199-214 (2000).
21. Motterlini, R., Foresti, R., Bassi, R. & Green, C. J. Curcumin, an antioxidant and anti-inflammatory agent, induces heme oxygenase-1 and protects endothelial cells against oxidative stress. Free Radic Biol Med 28, 1303-1312 (2000).
22. Planet, S., Guo, S., Kavanagh, K. T. & Sonenshein, G. E. Green tea polyphenol epigallocatechin-3 gallate inhibits 22. Her-2/neu signaling, proliferation, and transformed phenotype of breast cancer cells. Cancer Res 62, 652-655 (2002).
23. Farooqui, A. A., Ong, W. Y., Horrocks, L. A. & Farooqui, T. Brain Cytosolic Phospholipase A2: Localization, role, and involvement in neurological diseases. Neuroscientist 6, 169-180 (2000).
24. Victor, V. M., Rocha, R., Sola, E., Barfuls, C. & Hernandez-Milares, A. Oxidative stress, endothelial dysfunction and atherosclerosis. Curr Pharm Des 15, 2988-3002 (2009).
25. Fialkow, L., Wang, Y. & Downey, G. P. Reactive oxygen and nitrogen species as signaling molecules regulating neutrophil function. Free Radic Biol Med 42, 153-164 (2007).
26. Biewenga, G Ph, Haenen GRMM, Bast A. An overview of Lipoate Chemistry, Chapter 1 in: Lipoic Acid In Health & Disease. (Marcel Dekker Inc., New York; 1997).
27. Constantinescu, A. et al. Reduction and transport of lipoic acid by human erythrocytes. Biochem Pharmacol 50, 253-261 (1995).
28. Haramaki, N., Han, D., Handelman, G. J., Tritschler, H. J. & Packer, L. Cytosolic and mitochondrial systems for NADH- and NADPH-dependent reduction of alpha-lipoic acid. Free Radic Biol Med 22, 535-542 (1997).
29. Jones, W. et al. Uptake, recycling, and antioxidant actions of alpha-lipoic acid in endothelial cells. Free Radic Biol Med 33, 83-93 (2002).
30. Packer, L., Witt, E. H. & Tritschler, H. J. Alpha-Lipoic acid as a biological antioxidant. Free Radic Biol Med 19, 227-250 (1995).
31. Morcos, M. et al. Effect of alpha-lipoic acid on the progression of endothelial cell damage and albuminuria in patients with diabetes mellitus: an exploratory study. Diabetes Res Clin Pract 52, 175-183 (2005).
32. Mari, M., Morales, A., Colell, A., Garcia-Ruiz, C. & Fernandez-Checa, J. C. Mitochondrial glutathione, a key survival anti-oxidant. Antioxid Redox Signal 11, 2685-2700 (2009).
33. Mijnhout, G. S. et al. Alpha lipoic acid: a new treatment for neuropathic pain in patients with diabetes? Neth J Med 110, 158-162 (2010).
34. Ying, Z. et al. Lipoic acid effects on established atherosclerosis. Life Sci 86, 95-102 (2010).
35. Arner, E. S., Nordberg, J. & Holmgren, A. Efficient reduction of lipoamide and lipoic acid by mammalian thioredoxin reductase. Biochem Biophys Res Commun. 225, 268-274 (1996).
36. Teichert, J., Hermann, R., Ruus, P. & Preiss, R. Plasma kinetics, metabolism, and urinary excretion of alpha-lipoic acid following oral administration in healthy volunteers. J Clin Pharmacol 43, 1257-1267 (2003).
37. Sola, S. et al. Irbesartan and lipoic acid improve endothelial function and reduce markers of inflammation in the metabolic syndrome: results of the Irbesartan and Lipoic Acid in Endothelial Dysfunction (ISLAND) study. Circulation 111, 343-348 (2005).
38. Basu, K., Dasgupta, B., Bhattacharya, S. K. & Debnath, P. K. Chemistry and pharmacology of apocynin, isolated from *Picrorhiza kurroa*. Curr Sci 40, 603-604 (1971).
39. Mannick, E., Bravo, L. E., Zarama, G., Realpe, J. E. & Zhang, X-J. Inducible Nitric Oxide Synthase, Nitrotyrosine, and Apoptosis in *Helicobacter pylori* Gastritis: Effect of Antibiotics and Antioxidants. Cancer Res 56, 3238-3244 (1996).
40. Morley, J. E. The SAMP-8 mouse: a model of Alzheimer disease. Biogerontology 3, 57-60 (2002).
41. Butterfield, D. A. & Poon, H. F. The senescence-accelerated prone mouse (SAMP-8): a model of age-related cognitive decline with relevance to alterations of the gene expression and protein abnormalities in Alzheimer's disease. Exp Gerontology 40, 774-783 (2005).
42. Takahashi, R. & Goto, S. Altered gene expression in the brain of senescence accelerated mouse SAMP-8. International Congress Series 1240, 85-90 (2004).
43. Connell, B J., Saleh M C., Khan, B V., and Saleh T M. Lipoic acid protects against reperfusion injury in the early stages of cerebral ischemia. Brain Res., 1375:128-136, 2011.
44. Richard, M J P., Connell, B J., Khan B V., and Saleh T M. Cellular mechanisms by which lipoic acid confers protection during the early stages of cerebral ischemia. Neurosci. Res., 69:299-307, 2011.
45. Kanegae M P, Condino-Neto A, Pedroza L A, de Almeida A C, Rehder J, da Fonseca L M, Ximenes V F. Diapocynin versus apocynin as pretranscriptional inhibitors of NADPH oxidase and cytokine production by peripheral blood mononuclear cells. Biochem Biophys Res Commun. 2010 Mar. 12; 393(3):551-4. Epub 2010 Feb. 18.
46. Connell B J, Saleh T M. A novel rodent model of reperfusion injury following occlusion of the middle cerebral artery. *J Neurosci Methods* 190: 28-33, 2010.
47. Paxinos G, Watson C. *The Rat Brain in Stereotaxic Coordinates*. San Diego, Calif.: Academic Press, 1987.
48. Minnerup J, Schabitz W R. Multifunctional actions of approved and candidate stroke drugs. *Neurotherapeutics* 6: 43-52, 2009.
49. Di Stefano A, Sozio P, Cocco A, Iannitelli A, Santucci E, Costa M, Pecci L, Nasuti C, Cantalamessa F, Pinnen F. L-Dopa- and dopamine-R-α-Lipoic acid Conjugates as multifunctional codrugs with antioxidant properties. *J Med Chem* 49: 1486-1493, 2006.
50. Chen H, Song Y S, Chan P H. Inhibition of NADPH oxidase is neuroprotective after ischemia reperfusion. *J Cereb Blood Flow Metab* 29: 1262-1272, 2009.
51. Connell B J, Saleh M, Khan B V, Saleh T M. Apocynin may limit total cell death following cerebral ischemia and reperfusion by enhancing apoptosis. *Food Chem Toxicol* 49: 3063-3069, 2011.
52. Jackman K A, Miller A A, DeSilva T M, Crack P J, Drummond G R, Sobey C G. Reduction of cerebral infarct volume by apocynin requires pretreatment and is absent in Nox2-deficient mice. *Br J Pharmacol* 156: 680-688, 2009.
53. Tang X N, Cairns B, Cairns N, Yenari M A. Apocynin improves outcome in experimental stroke with a narrow dose range. *Neuroscience* 154: 556-562, 2008.
54. Tang L L, Ye K, Yang X F, Zheng J S. Apocynin attenuates cerebral infarction after transient focal ischaemia in rats. *J Int Med Res* 35: 517-522, 2007.
55. Wang Q, Tompkins K D, Simonya A, Korthuis R J. Apocynin protects against global cerebral ischemia-reperfusion-induced oxidative stress, and injury in the gerbil hippocampus. *Brain Res* 1090: 182-189, 2006.
56. Lakhan S E, Kirchgessner A, Hofer M. Inflammatory mechanisms in ischemic stroke: Therapeutic approaches. J Transl Med 7: 7-97, 2009.
57. Myers M G, Norris J W, Hachinski V C, Sole M J. Cardiac sequlae of acute stroke. *Stroke* 13: 838-842, 1982.

58. Oppenheimer S M, Cechetto D F, Hachinski V C. Cerebrogenic cardiac arrhythmias: cerebral electrocardiographic influences and their role in sudden death. *Arch Neurol* 47: 513-519, 1990.
59. Cechetto D F, Wilson J X, Smith K, Wolski D, Hachinski V C. Autonomic and myocardial changes in MCAO: stroke models in the rat. *Brain Res* 502: 296-305, 1989.
60. Billman G E, Schwartz T M, Stone H L. Baroreceptor control of heart rate: a predictor of sudden cardiac death. *Circulation* 66: 874-880, 1982.
61. Saleh T M, Cribb A E, Connell B J. Reduction in infarct size by local estrogen does not prevent autonomic dysfunction after stroke. *Am J Physiol Regul Integr Comp Physiol* 281: R2088-R2095, 2001.
62. Saleh T M, Connell B J, Cribb A E. Estrogen in the parabrachial nucleus attenuates the synpathoexcitation following MCAO in male rats. *Brain Res* 1066: 187-195, 2005.
63. Chan P H. Mitochondrial dysfunction and oxidative stress as determinants of cell death/survival in stroke. *Ann NY Acad Sci* 1042: 203-209, 2005.
64. Smith A R, Shenvi S V, Widlansky M, Suh J H, Hagen T. Lipoic acid as a potential therapy for chronic diseases associated with oxidative stress. *Curr Med Chem* 11: 1135-1146, 2004.
65. Packer L, Tritschler H J, Wessel K. Neuroprotection by the metabolic antioxidant α-lipoic acid. *Free Radic Biol Med* 22: 359-378, 1997.
66. Slemmer J E, Shacka J J, Sweeney M I, Weber J. Antioxidants and free radical scavengers for the treatment of stroke, traumatic brain injury and aging. *Curr Med Chem* 15: 404-414, 2008.
67. Pamplona R, Costantini D. Molecular and structural antioxidant defense against oxidative stress in animals. *Am J Physiol Regul Integr Comp Physiol* 301: R843-R863, 2011.
68. Candelario-Jalil E. Mhadu N H, Al-Dalain S M, Martinez G, Leon O S. Time course of oxidative damage in differing brain regions following transient cerebral ischemia in gerbils. *Neurosci Res* 41: 233-241, 2001.
69. Chan P H. Reactive oxygen radicals in signaling and damage in the ischemic brain. *J Cereb Blood Flow Metab* 21: 2-14, 2001.
70. Margaill I, Plotkine M, Lerouet D. Antioxidant strategies in the treatment of stroke. *Free Radic Biol Med* 39: 429-43, 2005.
71. Ginsberg M D. Current status of neuroprotection for cerebral ischemia: Synoptic overview. *Stroke* 40: S111-S114, 2008.
72. Mignini, F., M. Capacchietti, et al. (2011). "Single dose bioavailability and pharmacokinetic study of a innovative formulation of alpha-lipoic acid (ALA600) in healthy volunteers." Minerva Med 102(6): 475-482.
73. Zhang, Y. S., L. He, et al. (2012). "A novel pathway of NADPH oxidase/vascular peroxidase 1 in mediating oxidative injury following ischemia-reperfusion." Basic Res Cardiol 107(3): 266.
74. Connell, B. J. and T. M. Saleh (2012). "Co-administration of apocynin with lipoic acid enhances neuroprotection in a rat model of ischemia/reperfusion." Neurosci Lett 507(1): 43-46.

We claim:
1. A compound of Formula I:

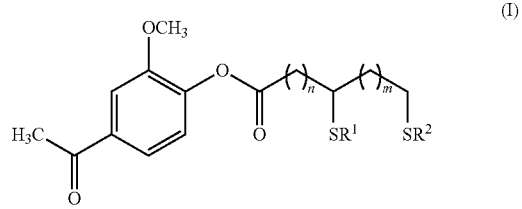

wherein
n is 1, 2, 3, 4, 5 or 6;
m is 0, 1 or 2;
$R^1$ and $R^2$ are independently selected from the group consisting of H, $C_{1-6}$alkyl and $C(O)C_{1-6}$alkyl, or
$R^1$ and $R^2$ are absent and the two sulfur atoms are bonded together to form, together with the carbon atoms between them, a 4, 5 or 6 membered ring, or a pharmaceutically acceptable salt and/or solvate thereof.
2. The compound of claim 1, wherein n is 3, 4 or 5.
3. The compound of claim 2, wherein n is 4.
4. The compound of claim 1, wherein m is 1 or 2.
5. The compound of claim 4, wherein m is 2.
6. The compound of claim 1, wherein $R^1$ and $R^2$ are independently selected from the group consisting of H, $C_{1-4}$alkyl and $C(O)C_{1-4}$alkyl.
7. The compound of claim 6, wherein $R^1$ and $R^2$ are independently selected from the group consisting of H, $CH_3$ and $C(O)CH_3$.
8. The compound of claim 6, wherein $R^1$ and $R^2$ are the same.
9. The compound of claim 8, wherein $R^1$ and $R^2$ are both H.
10. The compound of claim 1, wherein $R^1$ and $R^2$ are absent and the two sulfur atoms are bonded together to form, together with the carbon atoms between them, a 5 or 6 membered ring.
11. The compound of claim 10, wherein $R^1$ and $R^2$ are absent and the two sulfur atoms are bonded together to form, together with the carbon atoms between them, a 5 membered ring.
12. The compound of claim 1, wherein the compound of Formula I is selected from:

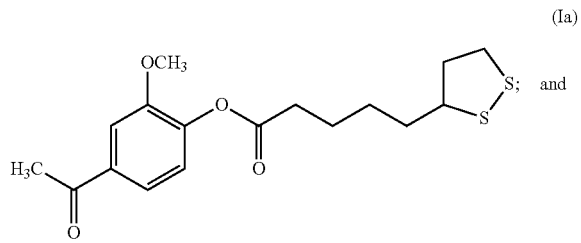

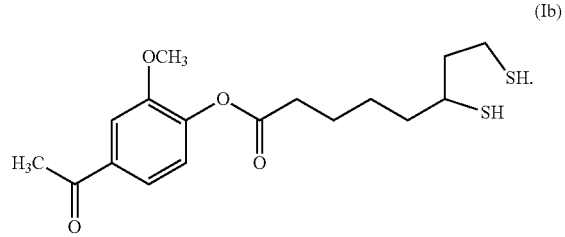

13. The compound of claim 1, wherein the compound of Formula I is:

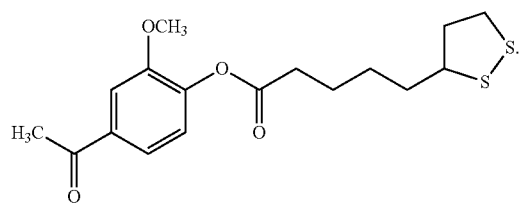

(Ia)

14. A pharmaceutical composition comprising one or more compounds of claim 1 and a pharmaceutically acceptable carrier.

15. A method for treating diseases, disorders or conditions mediated by oxidative stress comprising administering a therapeutically effective amount of one or more compounds of claim 1 to a subject in need thereof.

16. The method of claim 15, wherein the diseases, disorders or conditions mediated by oxidative stress are selected from reperfusion injury following stroke, neurodegenerative diseases, inflammatory diseases and neurovascular disorders.

17. The method of claim 16, wherein the neurodegenerative diseases are selected from dementia, Multiple Sclerosis and Parkinson's disease.

18. The method of claim 16, wherein the neurovascular disorders are selected from stroke, myocardial infarction, heart failure and renal failure.

19. The method of claim 16, wherein the inflammatory diseases or disorders are selected from collagen vascular diseases, metabolic disorders and cardiac disease.

* * * * *